(12) United States Patent
Shyur et al.

(10) Patent No.: US 8,754,121 B2
(45) Date of Patent: Jun. 17, 2014

(54) USE OF DEOXYELEPHANTOPIN (DET) AND ANALOGUES THEREOF FOR TREATMENT OF MELANOMA

(75) Inventors: Lie-Fen Shyur, Taipei (TW); Wen-Wan Chao, Changhua County (TW); Ya-Wen Cheng, Taipei (TW)

(73) Assignee: Academia Sinica, Taipei (TW)

( * ) Notice: Subject to any disclaimer, the term of this patent is extended or adjusted under 35 U.S.C. 154(b) by 198 days.

(21) Appl. No.: 13/213,897

(22) Filed: Aug. 19, 2011

(65) Prior Publication Data

US 2012/0045519 A1 Feb. 23, 2012

Related U.S. Application Data

(60) Provisional application No. 61/375,538, filed on Aug. 20, 2010.

(51) Int. Cl.

| | |
|---|---|
| *A61K 31/34* | (2006.01) |
| *A61K 33/24* | (2006.01) |
| *A61K 33/36* | (2006.01) |
| *A61K 31/19* | (2006.01) |
| *A61K 31/28* | (2006.01) |
| *A61K 31/35* | (2006.01) |
| *A61K 31/44* | (2006.01) |
| *A61K 31/56* | (2006.01) |
| *A61K 31/66* | (2006.01) |
| *A61K 31/69* | (2006.01) |
| *A61K 31/70* | (2006.01) |
| *A61K 31/135* | (2006.01) |
| *A61K 31/175* | (2006.01) |
| *A61K 31/335* | (2006.01) |
| *A61K 31/415* | (2006.01) |
| *A61K 31/445* | (2006.01) |
| *A61K 31/497* | (2006.01) |
| *A61K 31/505* | (2006.01) |

(52) U.S. Cl.
USPC ........... 514/468; 424/623; 424/649; 424/725; 514/34; 514/64; 514/107; 514/171; 514/252.18; 514/269; 514/283; 514/302; 514/323; 514/350; 514/393; 514/398; 514/406; 514/449; 514/459; 514/492; 514/578; 514/589; 514/648; 514/654; 514/922

(58) Field of Classification Search
USPC ........ 514/468, 34, 64, 107, 171, 252.18, 269, 514/283, 302, 323, 350, 393, 398, 406, 449, 514/459, 492, 578, 589, 648, 654, 922; 424/623, 649, 725
See application file for complete search history.

(56) References Cited

U.S. PATENT DOCUMENTS

2008/0003189 A1* 1/2008 Umishio et al. ................ 424/62

OTHER PUBLICATIONS

Wan Yong Ho, Huynh Ky, Swee Keong Yeap, Raha Abdul Rahim, Abdul Rahman Omar, Chai Ling Ho and Noorjahan Banu Alitheen, "Traditional practice, bioactivities and commercialization potential of *Elephantopus scaber* Linn.", Journal of Medicinal Plants Research vol. 3(13), pp. 1212-1221, Dec. 2009.*
Ni Ni Than, Serge Fotso, Madhumati Sevvana, George M. Sheldrick, Heinz H. Fiebig, Gerhard Kelter and Hartmut Laatsch, "Sesquiterpene Lactones from *Elephantopus scaber*", Z. Naturforsch. 60b, 200-204 (2005).*
Boulikas T and Vougiouka M., "Recent clinical trials using cisplatin, carboplatin and their combination chemotherapy drugs (review)" Oncology Reports Mar. 2004;11(3):559-95.*
Sewa S. Legha, Sigrid Ring, Nicholas Papadopoulos, Carl Plager, Sant Chawla and Robert Benjamin, "A Prospective Evaluation of a Triple-Drug Regimen Containing Cisplatin, Vinblastine, and Dacarbazine (CVD) for Metastatic Melanoma", Cancer 64:2024-2029, 1989.*
G. Xu, Q. Liang, Z. Gong, W. Yu, S. He and L. Xi, "Antitumor activities of the four sesquiterpene lactones from *Elephantopus scaber* L.", Experimental Oncology 28, 106-109, Jun. 2006.*
Huang et al. (2010) "Deoxyelephantopin, a novel multifunctional agent, suppresses mammary tumour growth and lung metastasis and doubles survival time in mice" British Journal of Pharmacology 159, 856-871.
Lee et al. (2010) "Differential Proteomic Profiling Identifies Novel Molecular Targets of Paclitaxel and Phytoagent Deoxyelephantopin against Mammary Adenocarcinoma Cells" Journal of Proteome Research 9, 237-253 237.

* cited by examiner

*Primary Examiner* — John Pak
*Assistant Examiner* — Nathan W Schlientz
(74) *Attorney, Agent, or Firm* — Hsiu-Ming Saunders; Intellectual Property Connections, Inc.

(57) ABSTRACT

Methods for treating melanoma in a subject in need thereof are disclosed. The method comprises administering to the subject a composition comprising a therapeutically effective amount of deoxyelephantopin or an analogue thereof; and a pharmaceutically acceptable carrier. Methods of inhibiting proliferation, migration and/or metastasis of melanoma cells in a subject in need thereof are also disclosed. Also disclosed are methods for reducing side effects of an anti-cancer agent in a subject in need thereof.

11 Claims, 34 Drawing Sheets

FIG. 1A
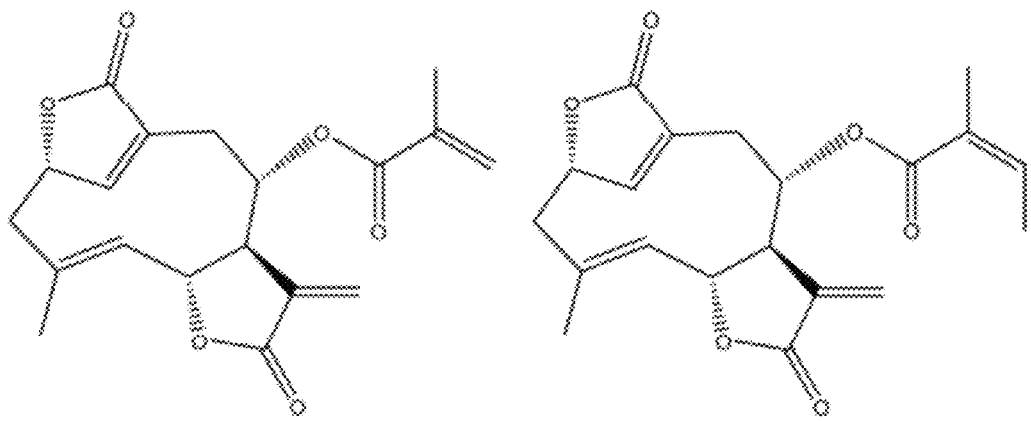
Isodeoxyelephantopin    Scabertopin
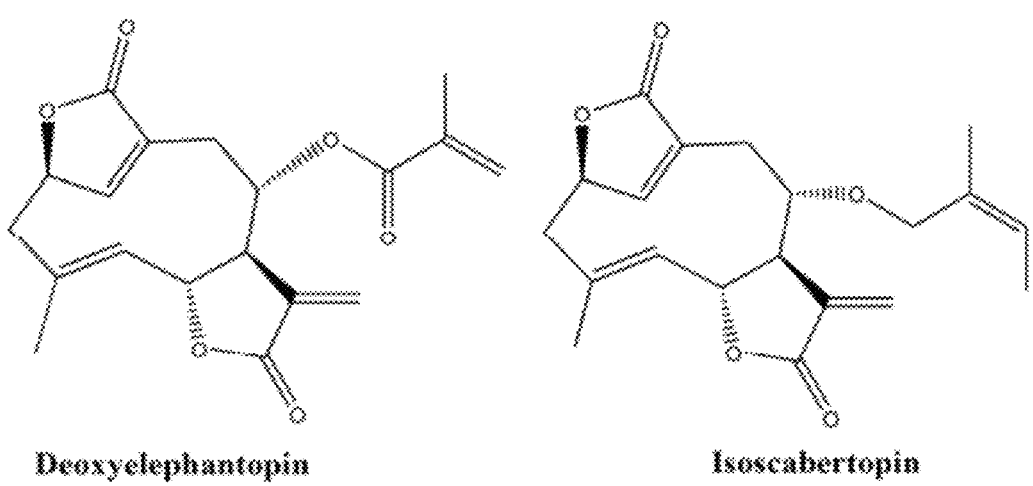
Deoxyelephantopin    Isoscabertopin
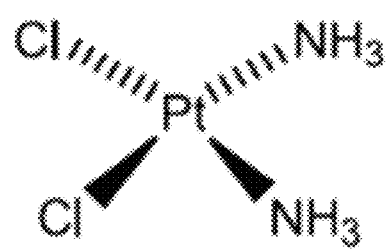
Cisplatin (CP)

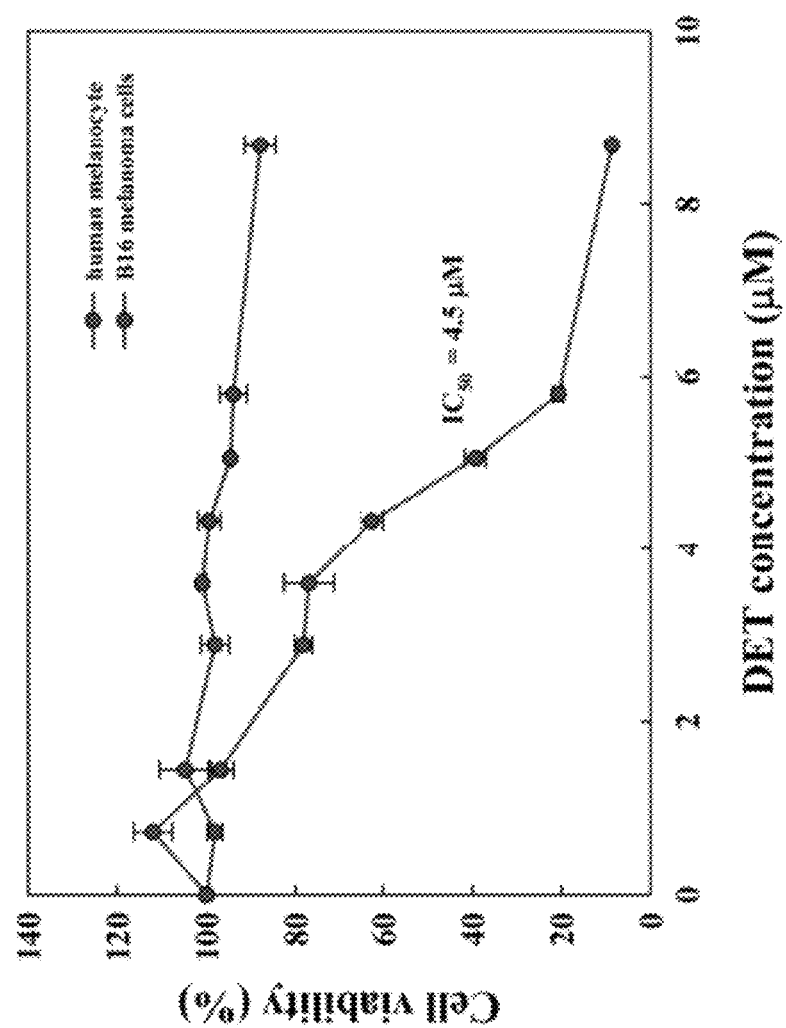
FIG. 1B1

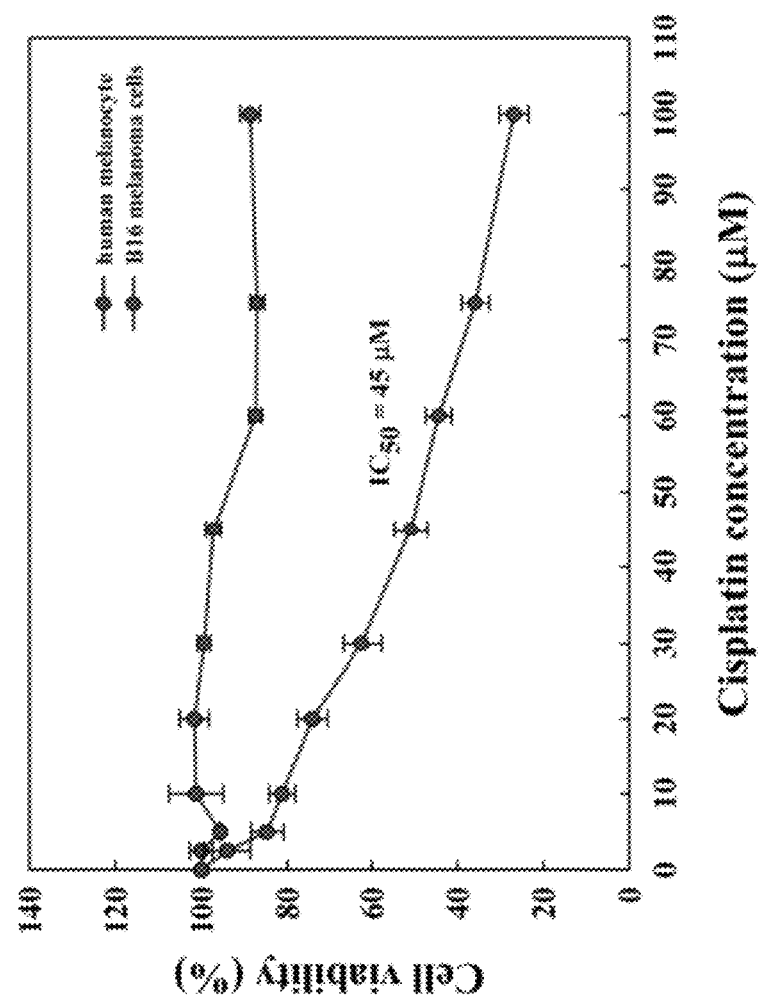
FIG. 1B2

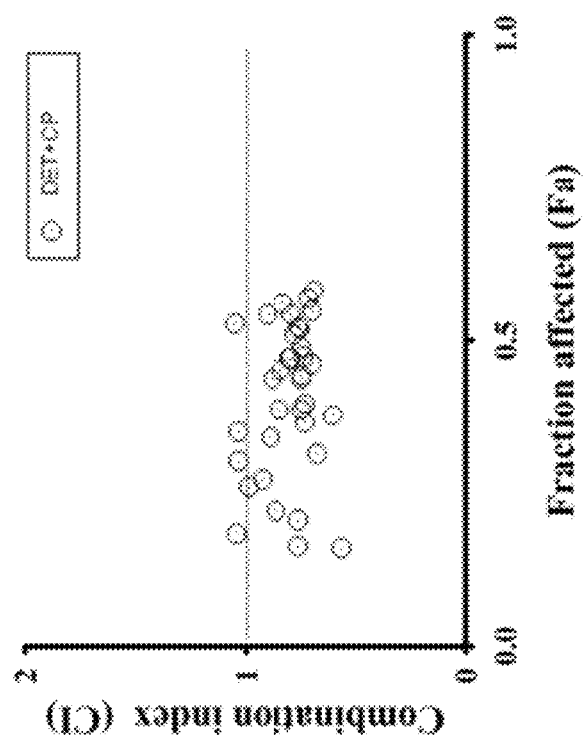
FIG. 1C2
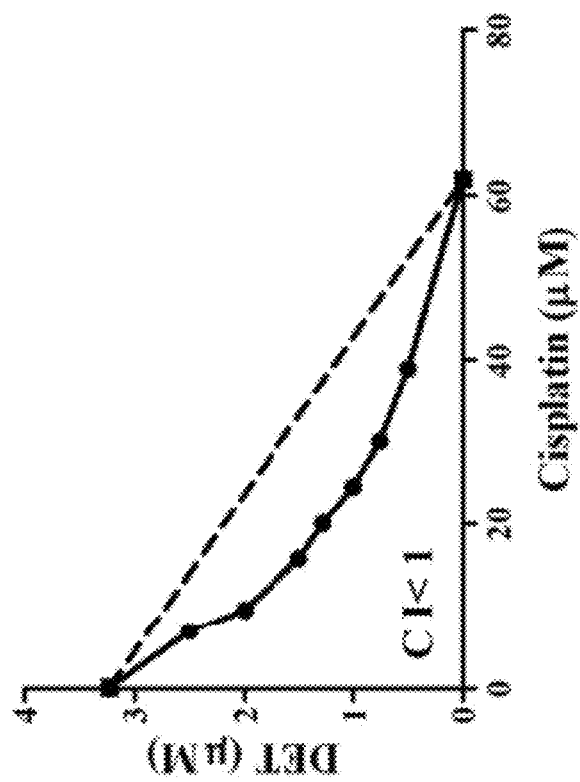
FIG. 1C1

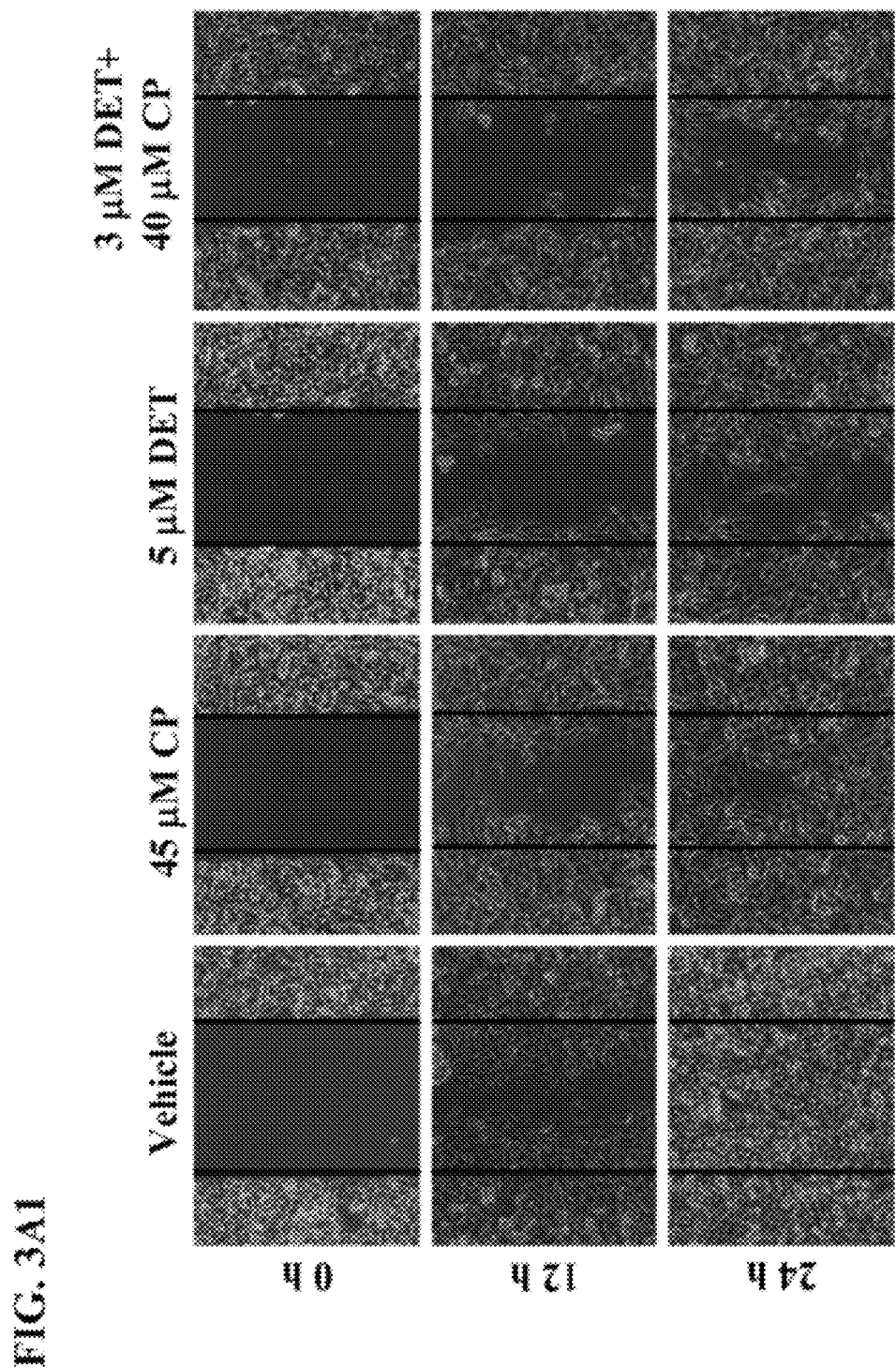
FIG. 3A1

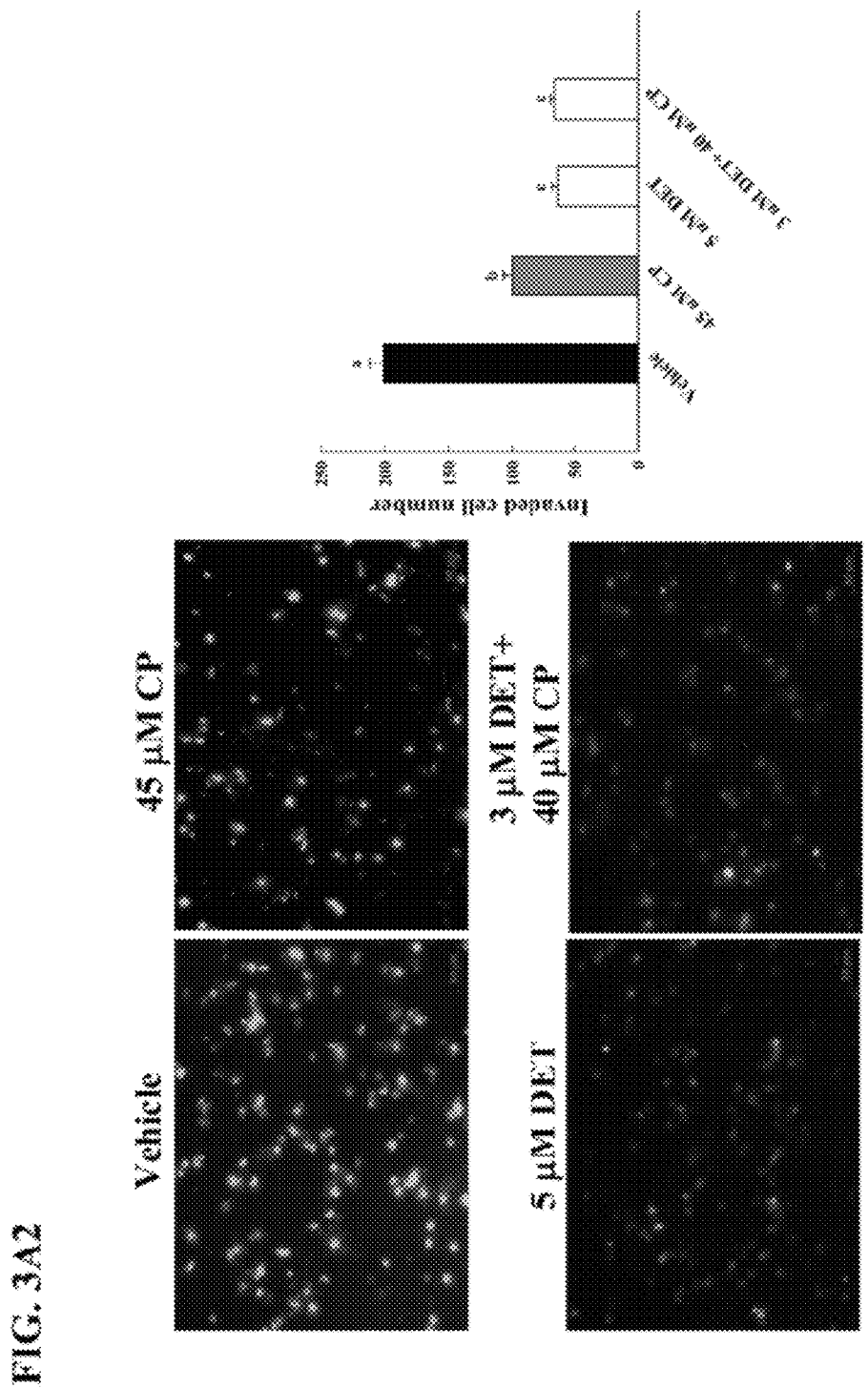
FIG. 3A2

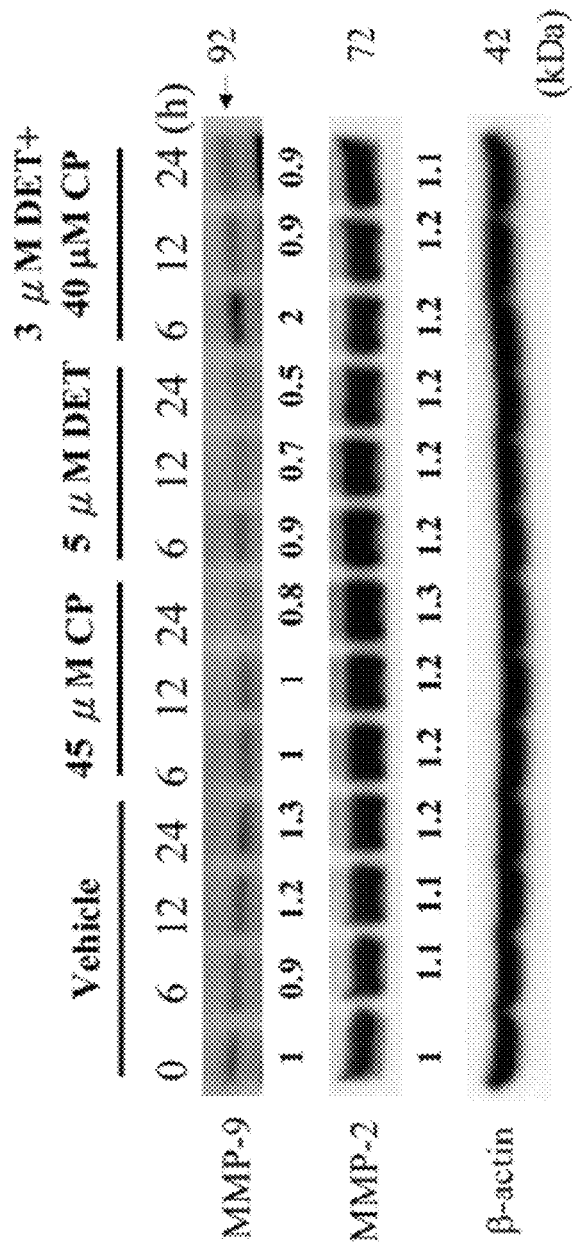
FIG. 3B1

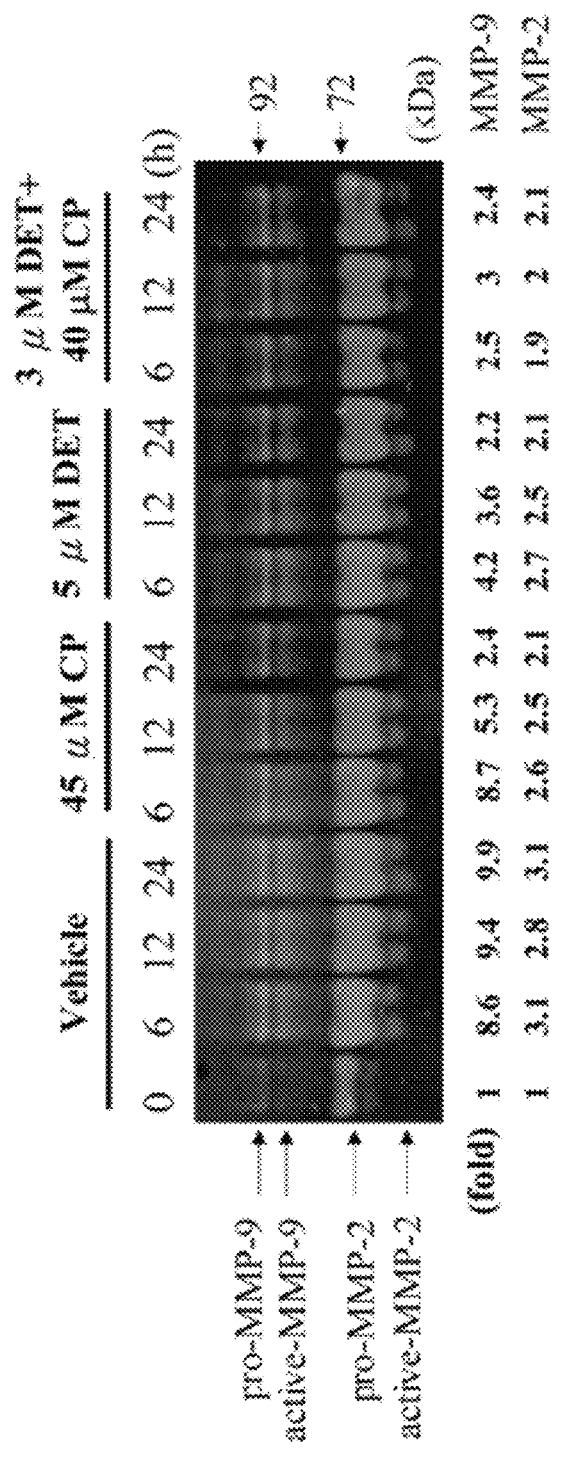
FIG. 3B2

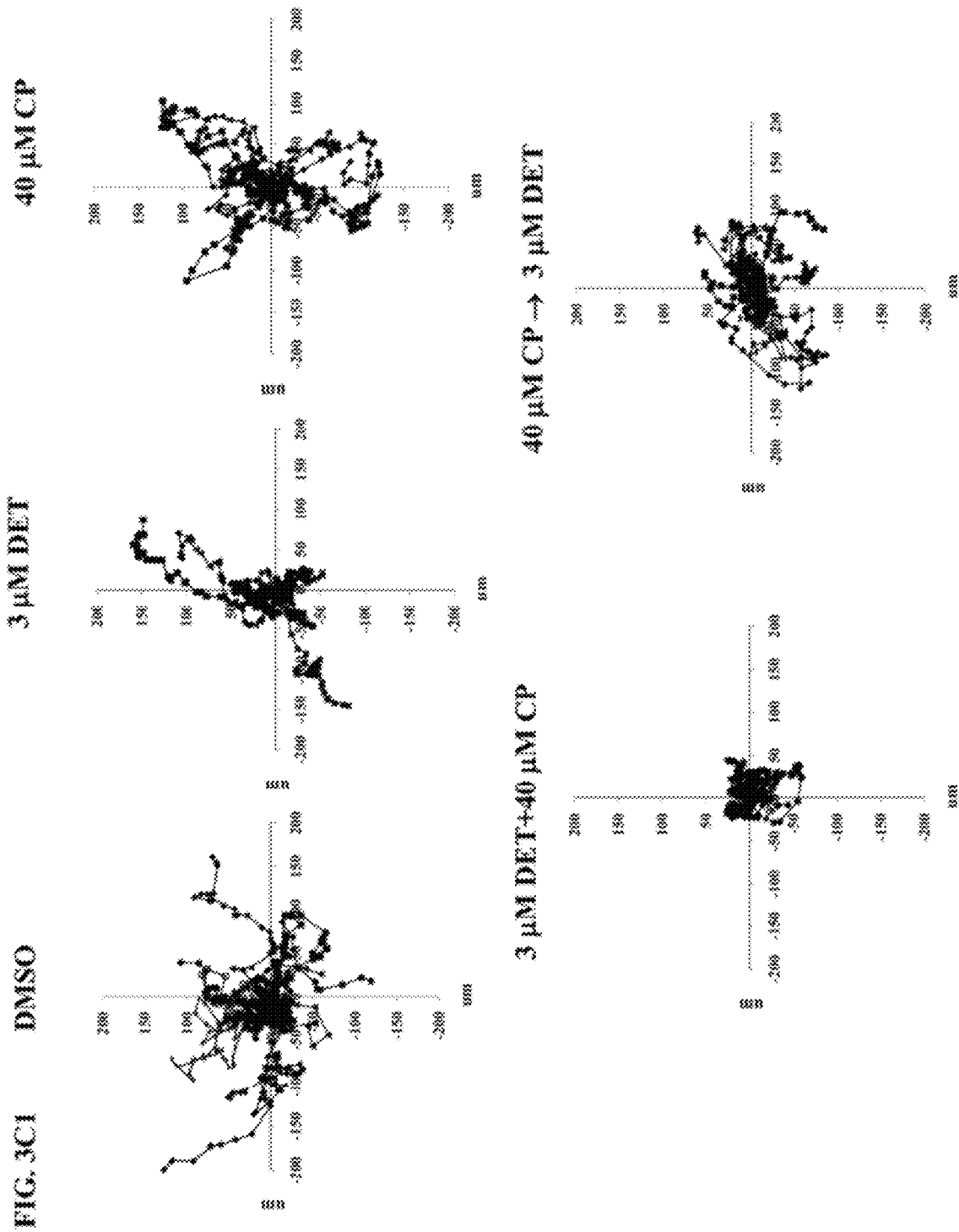
FIG. 3C1

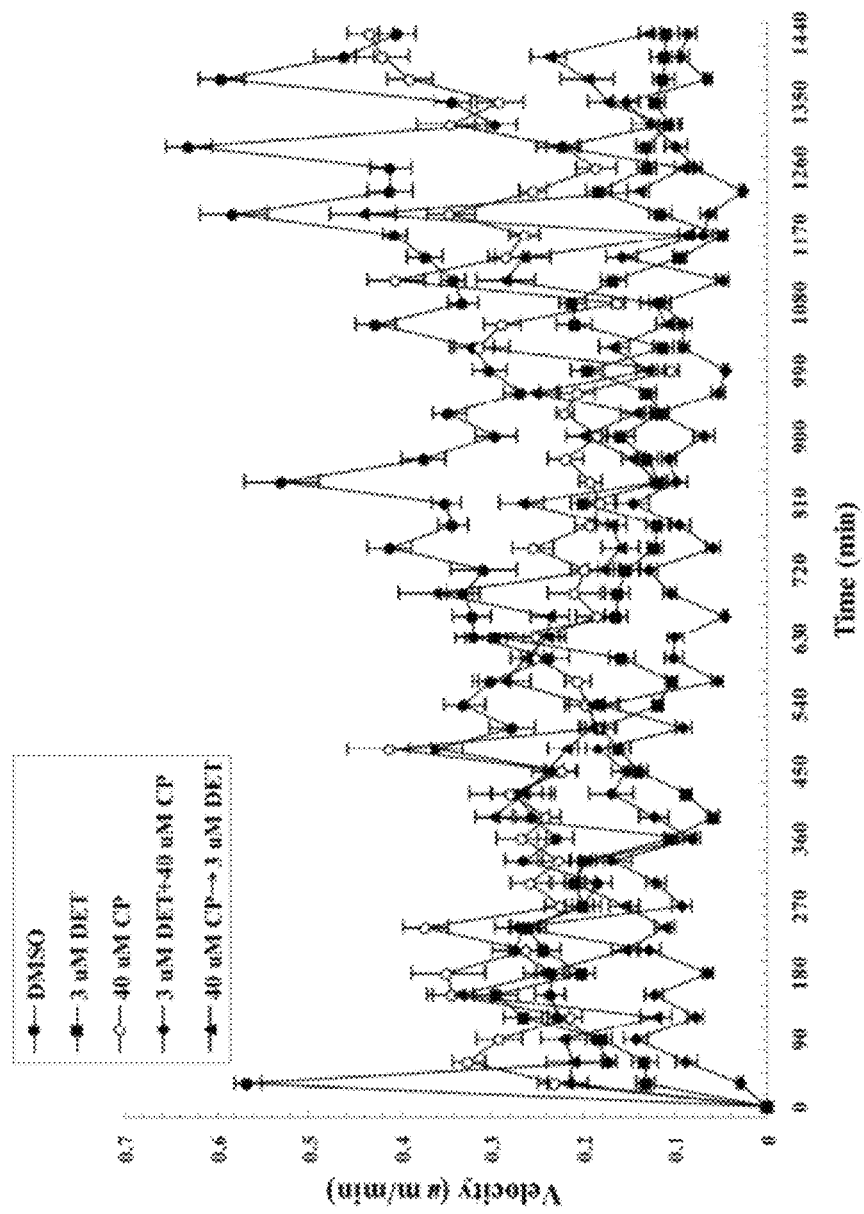
FIG. 3C2

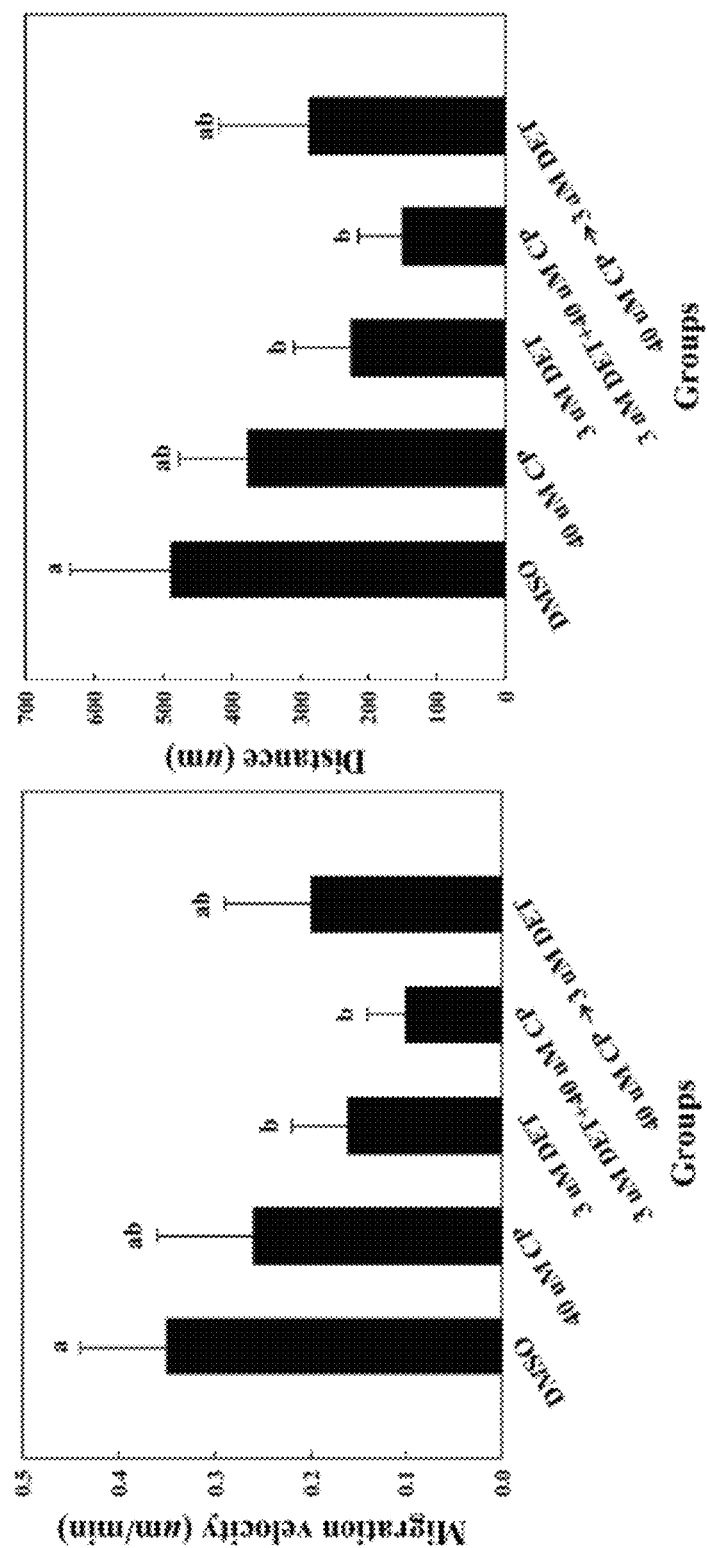
FIG. 3C3

FIG. 4A1
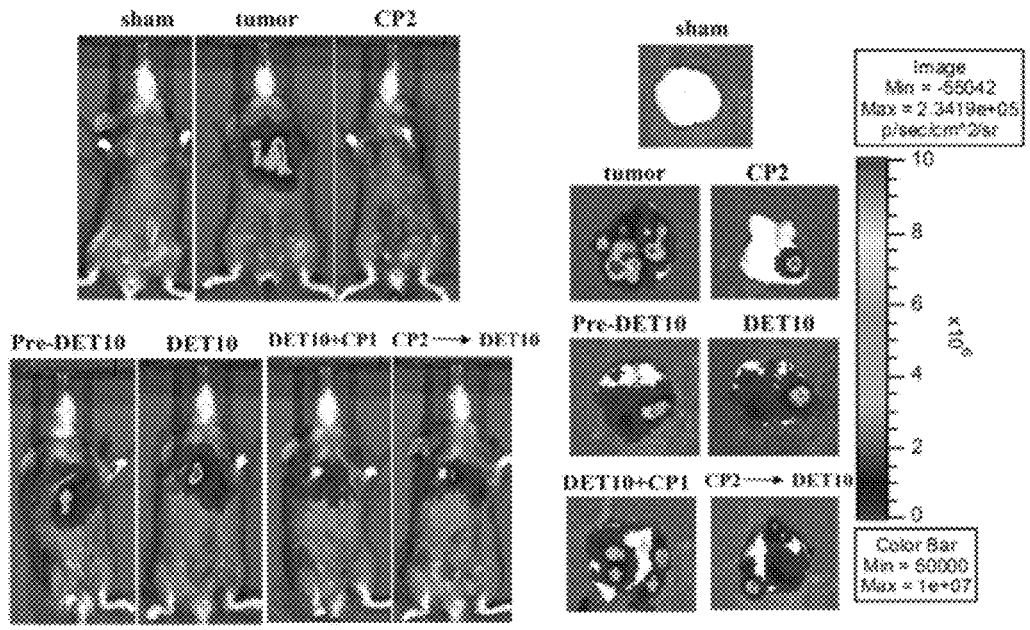
FIG. 4A2
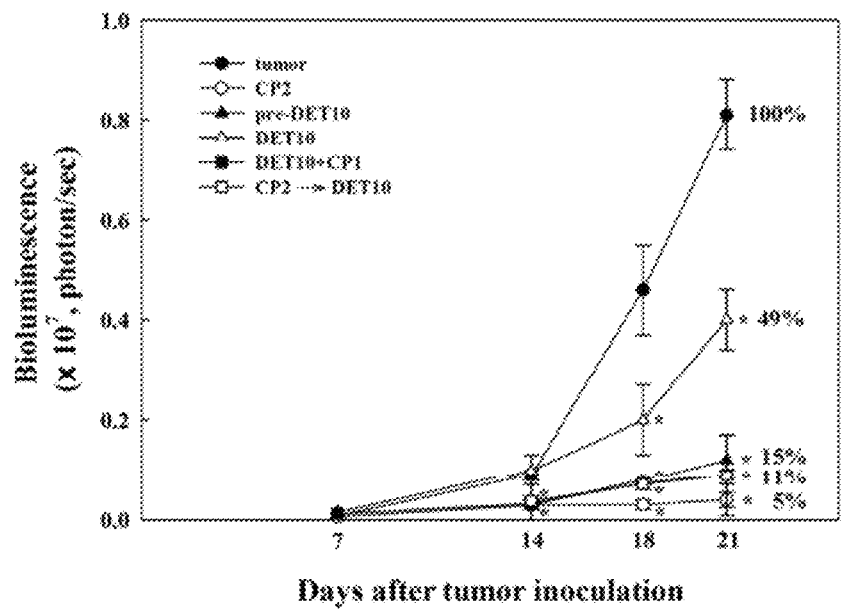

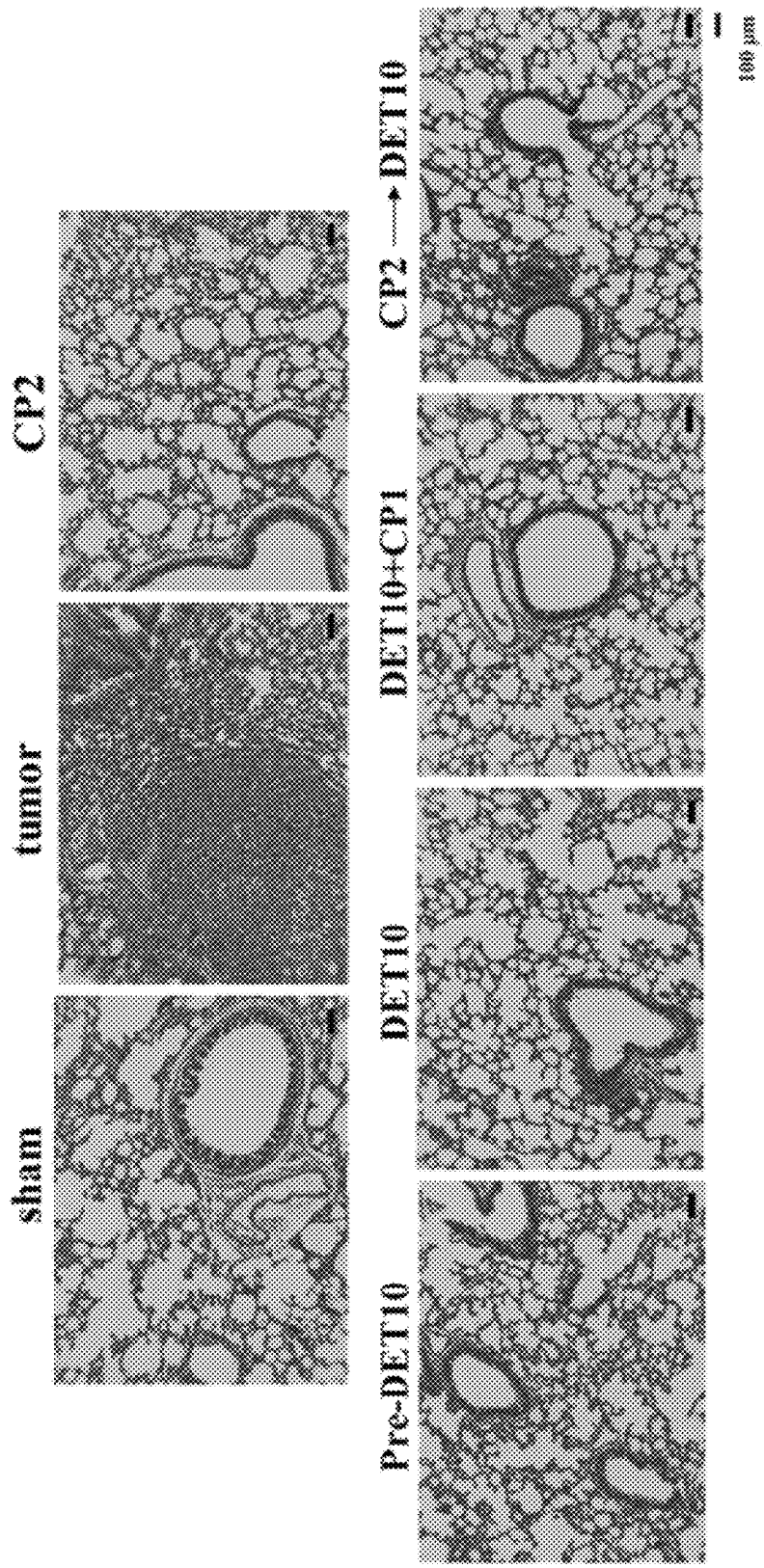
FIG. 4B1

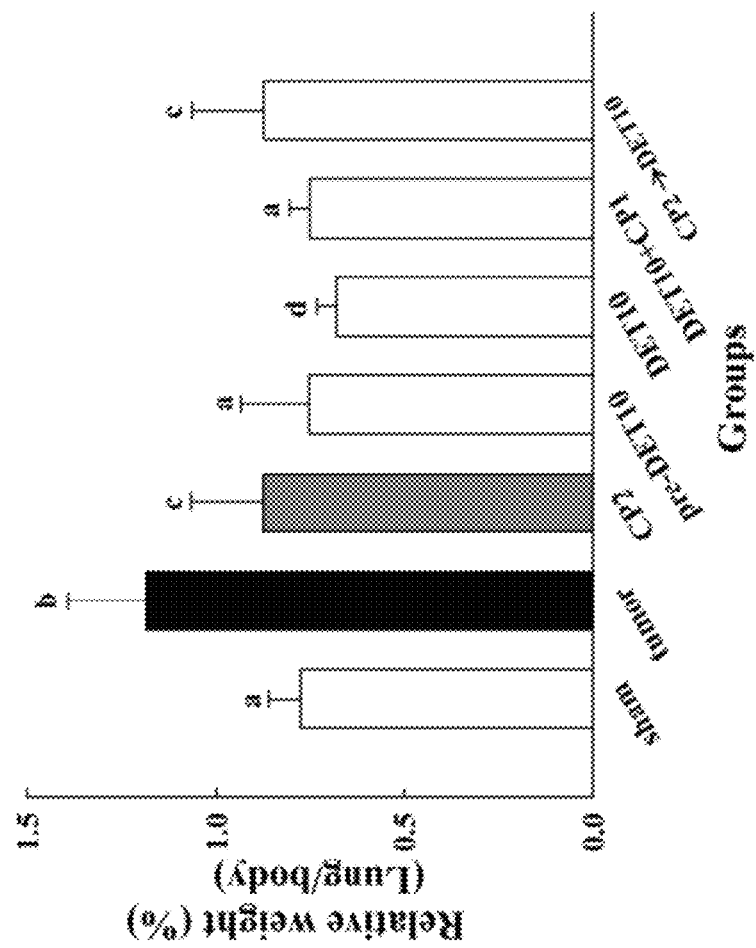
FIG. 4B2

FIG. 4C1
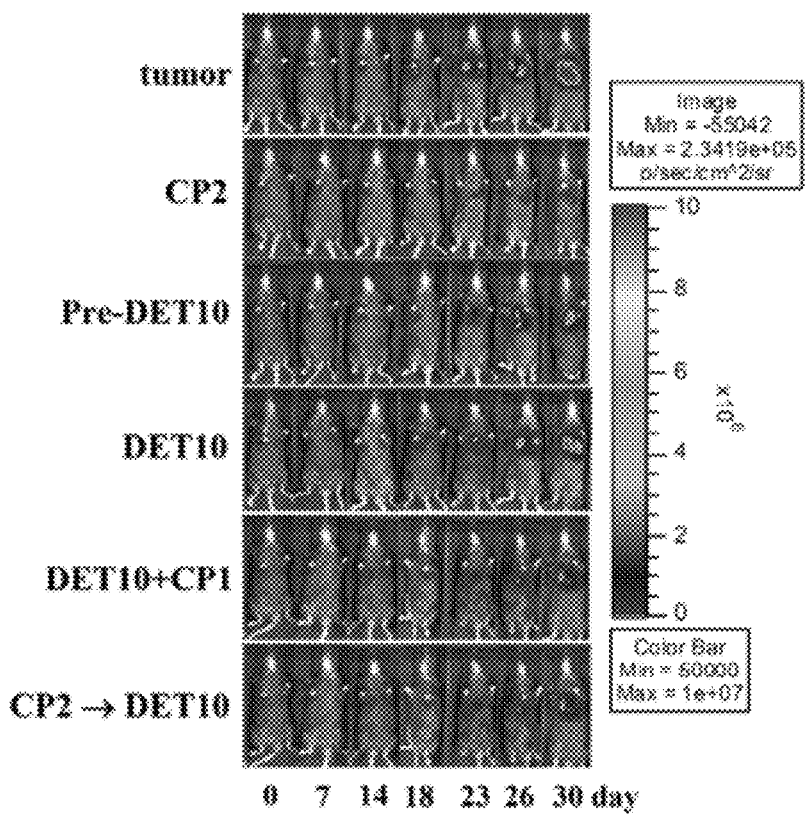
FIG. 4C2
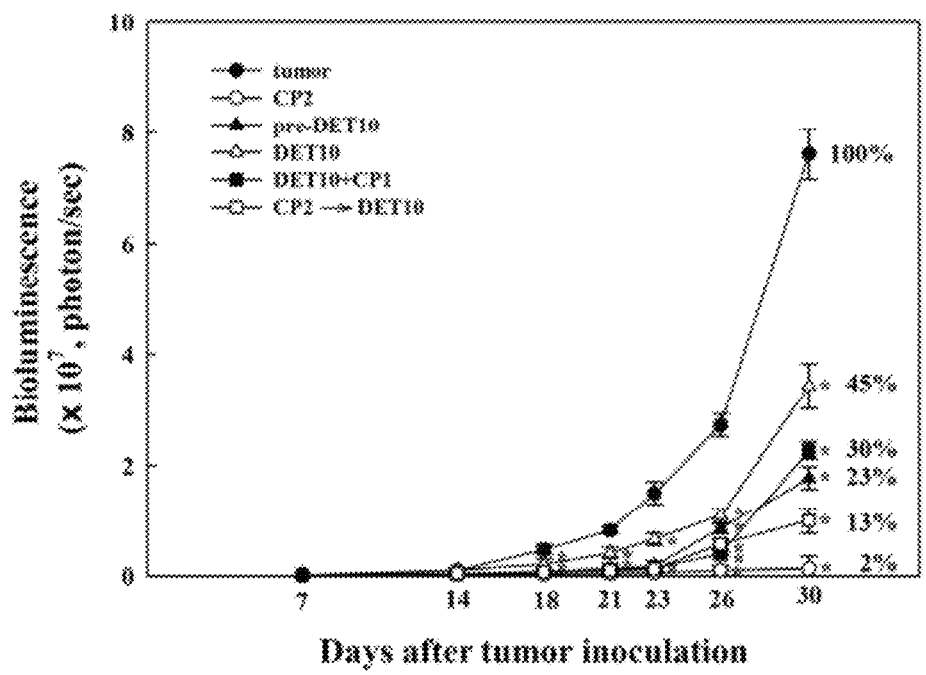

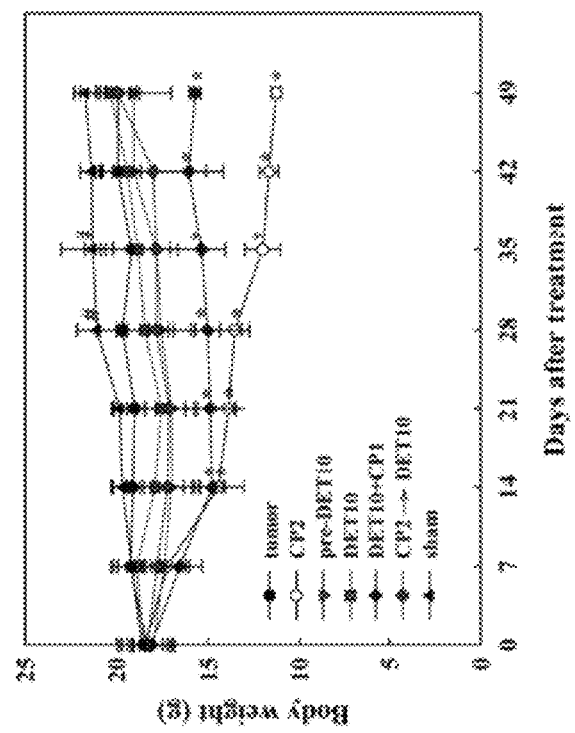
FIG. 4D2
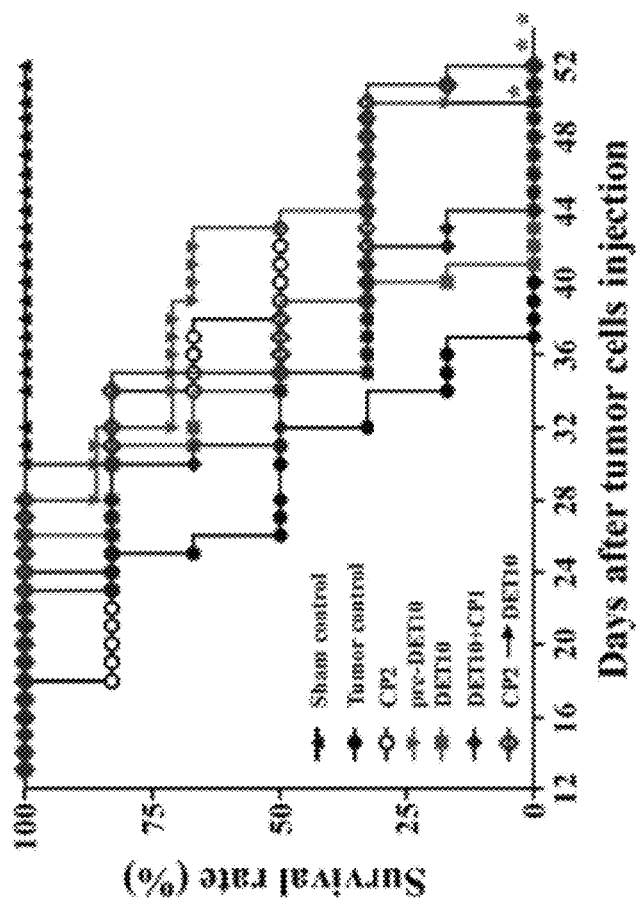
FIG. 4D1

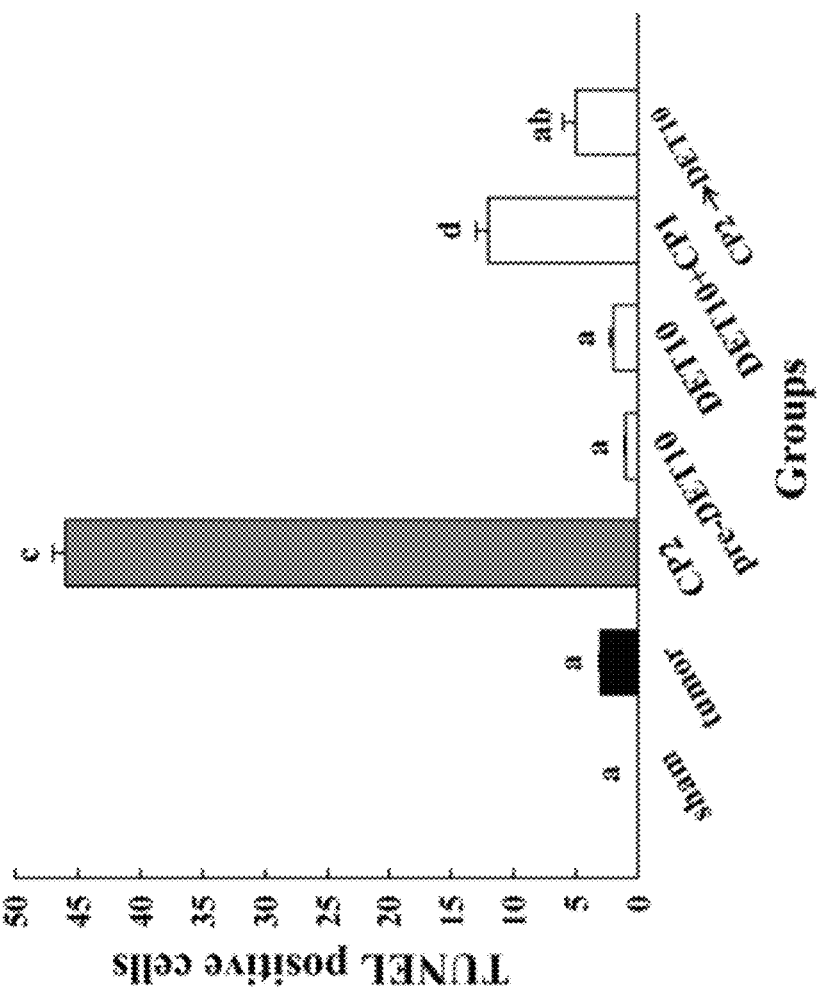
FIG. 5C1

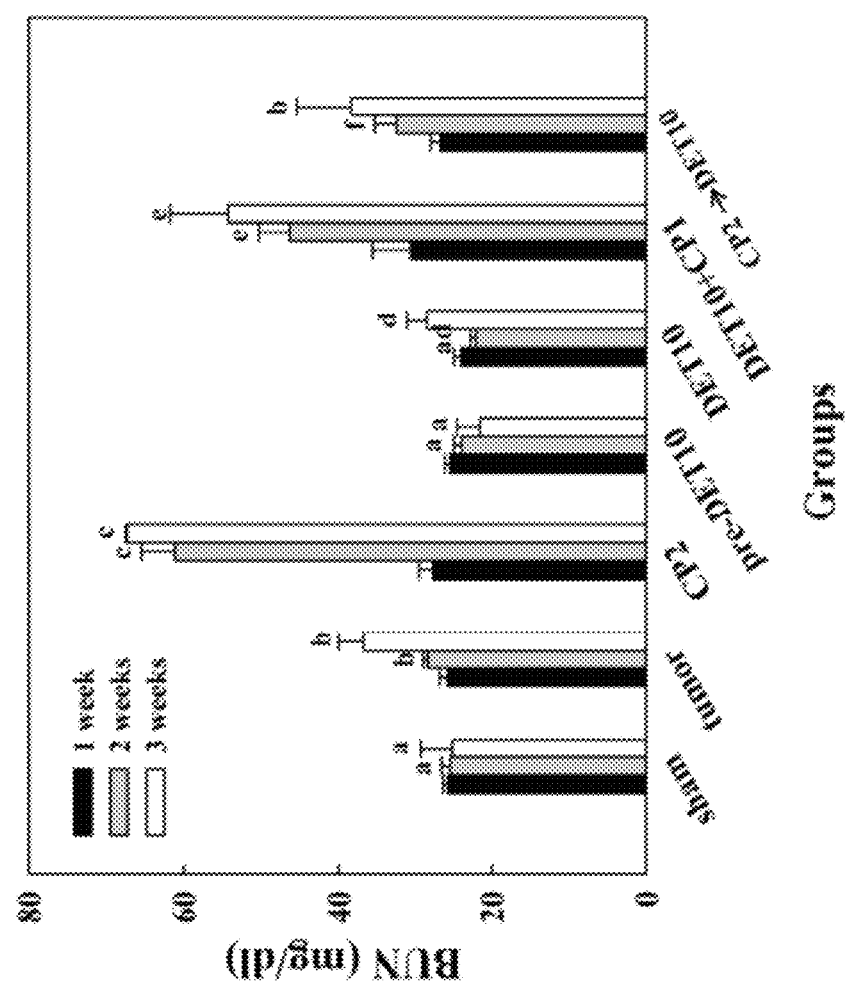
FIG. 5C2

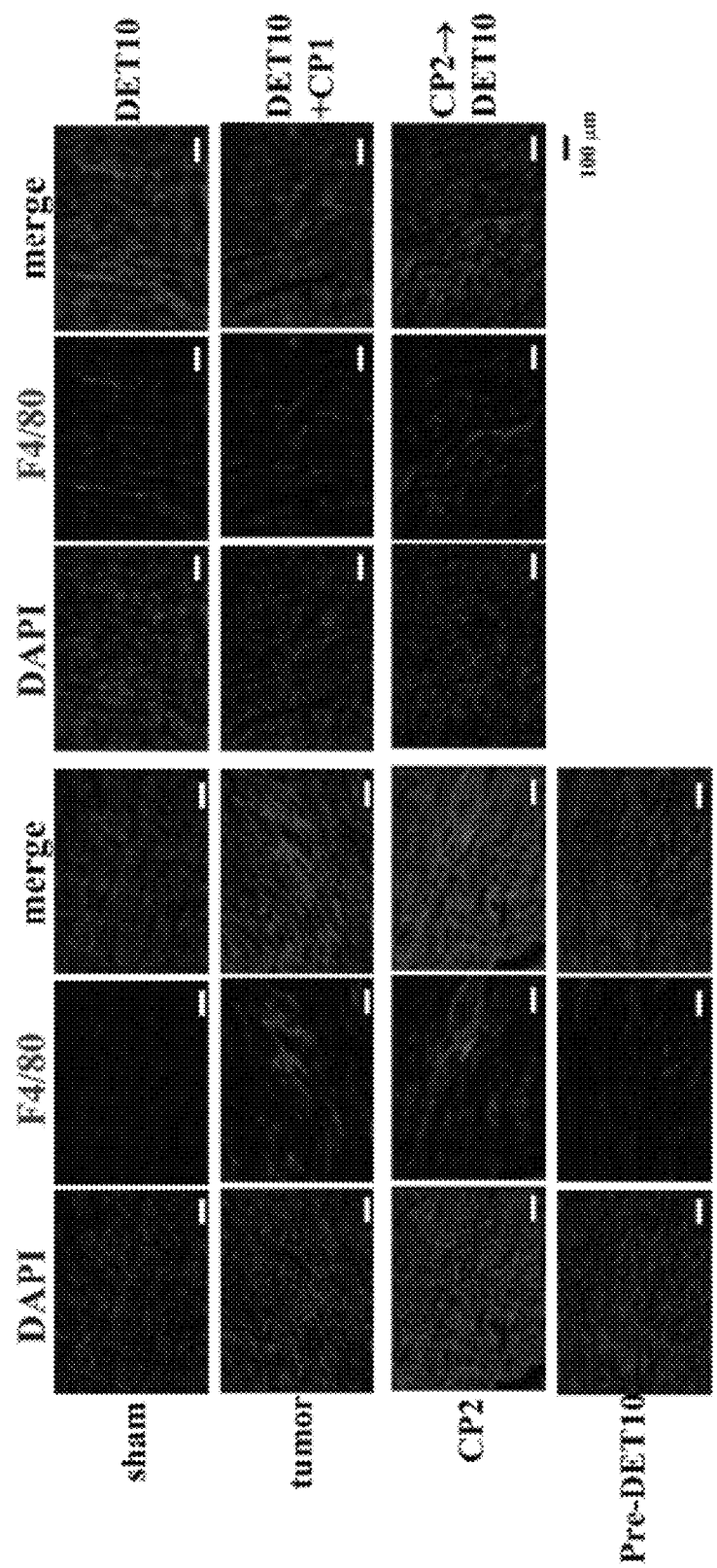
FIG. 5D1

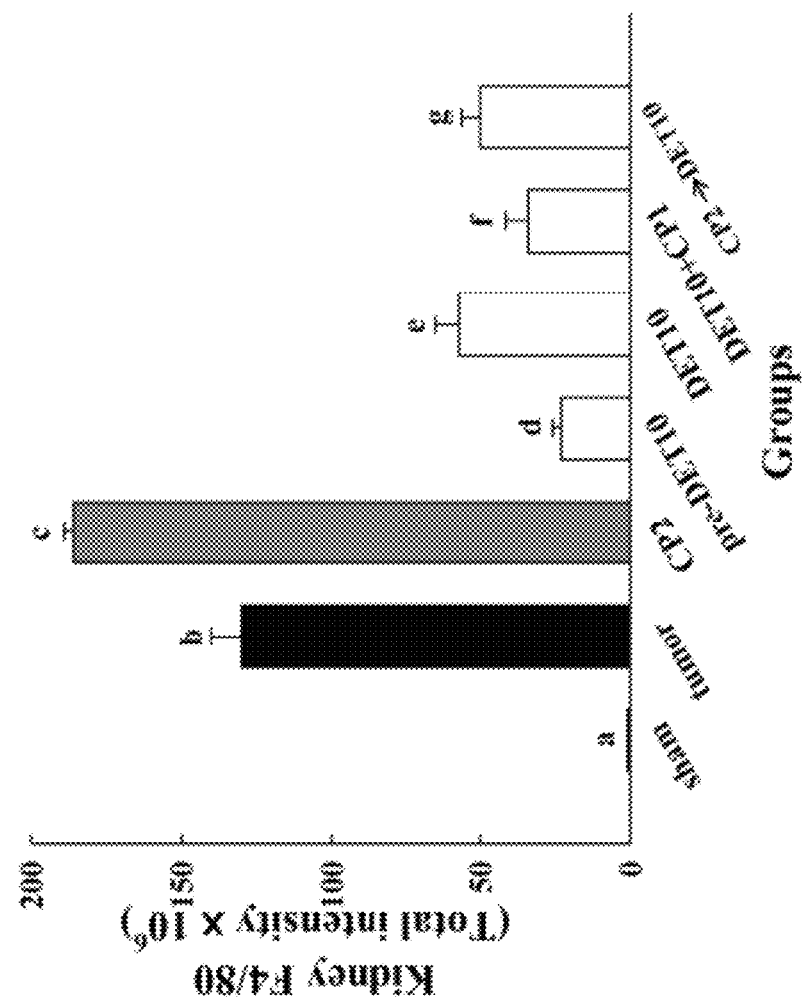
FIG. 5D2

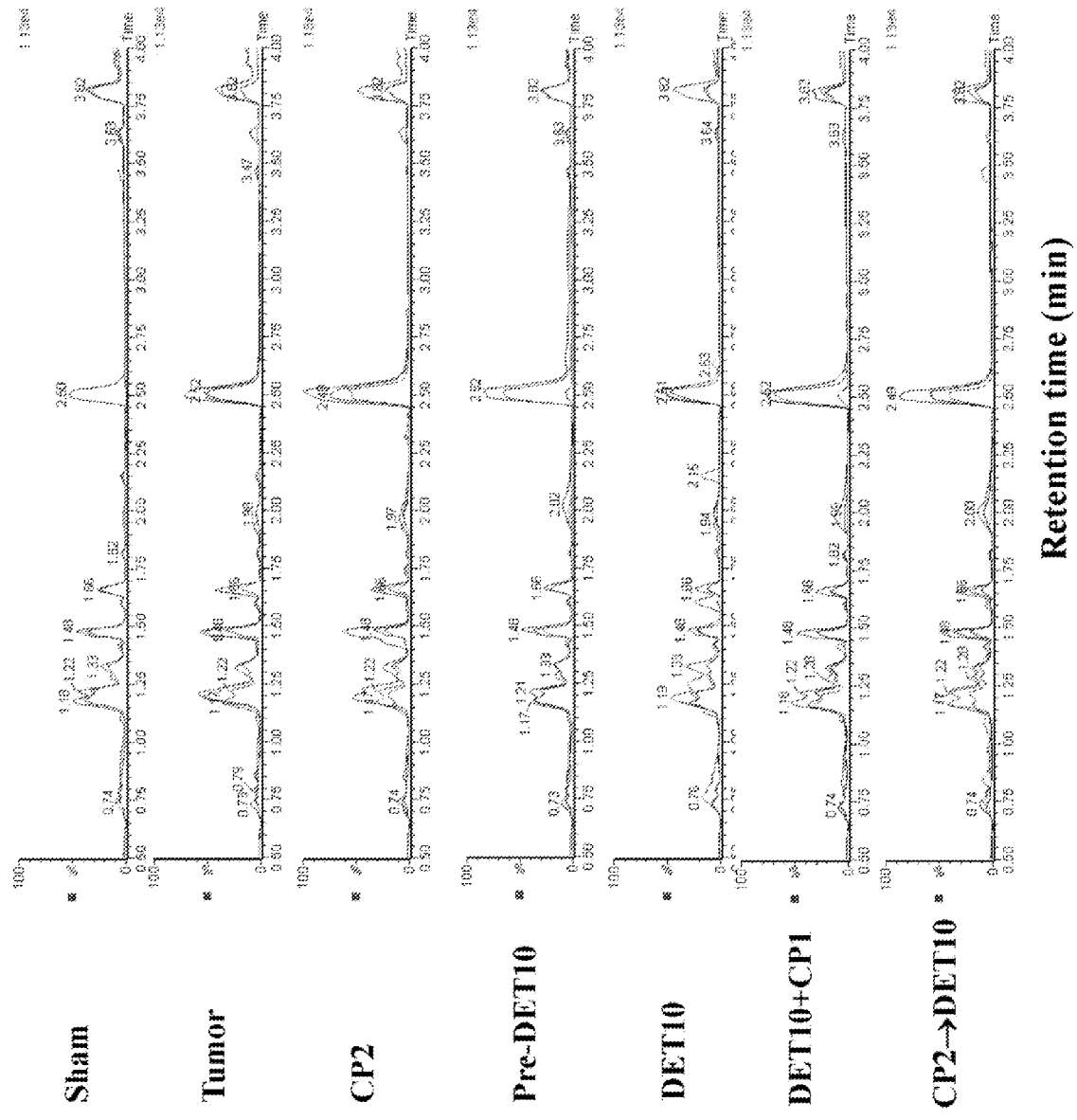

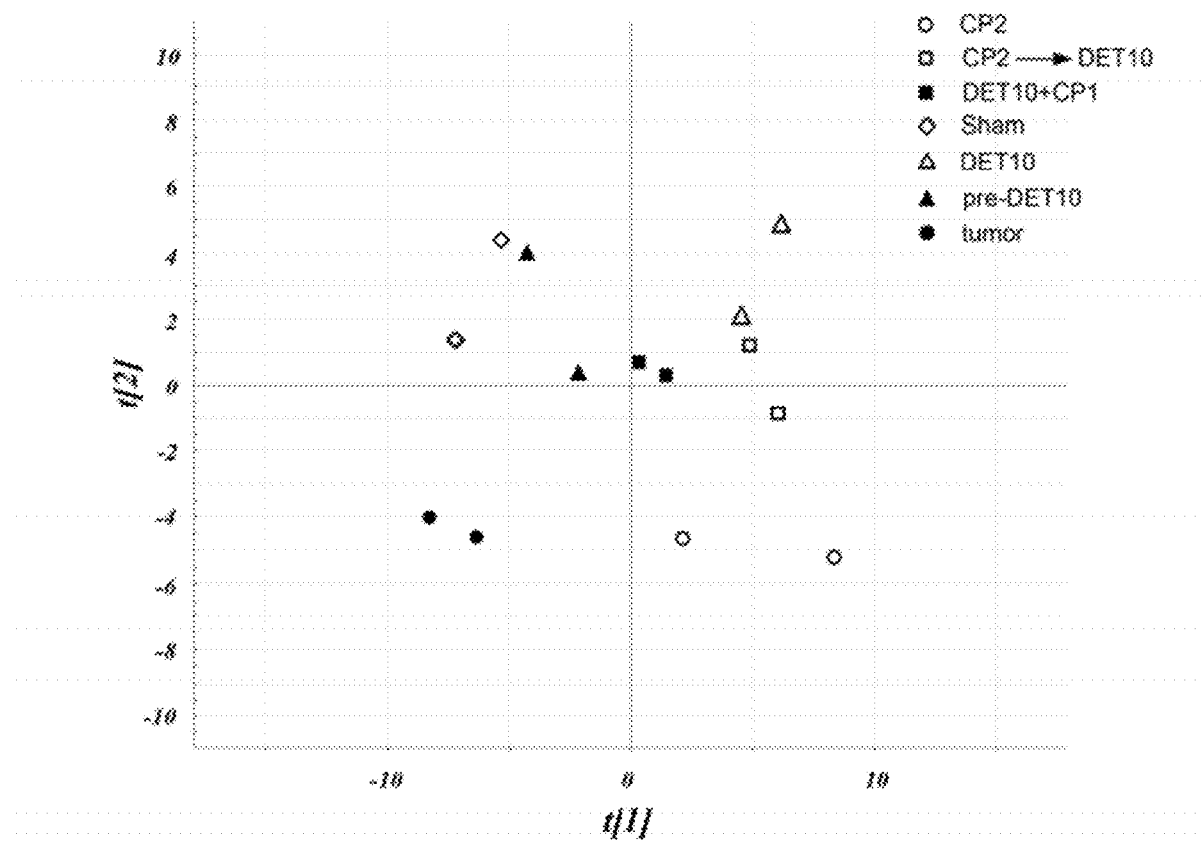

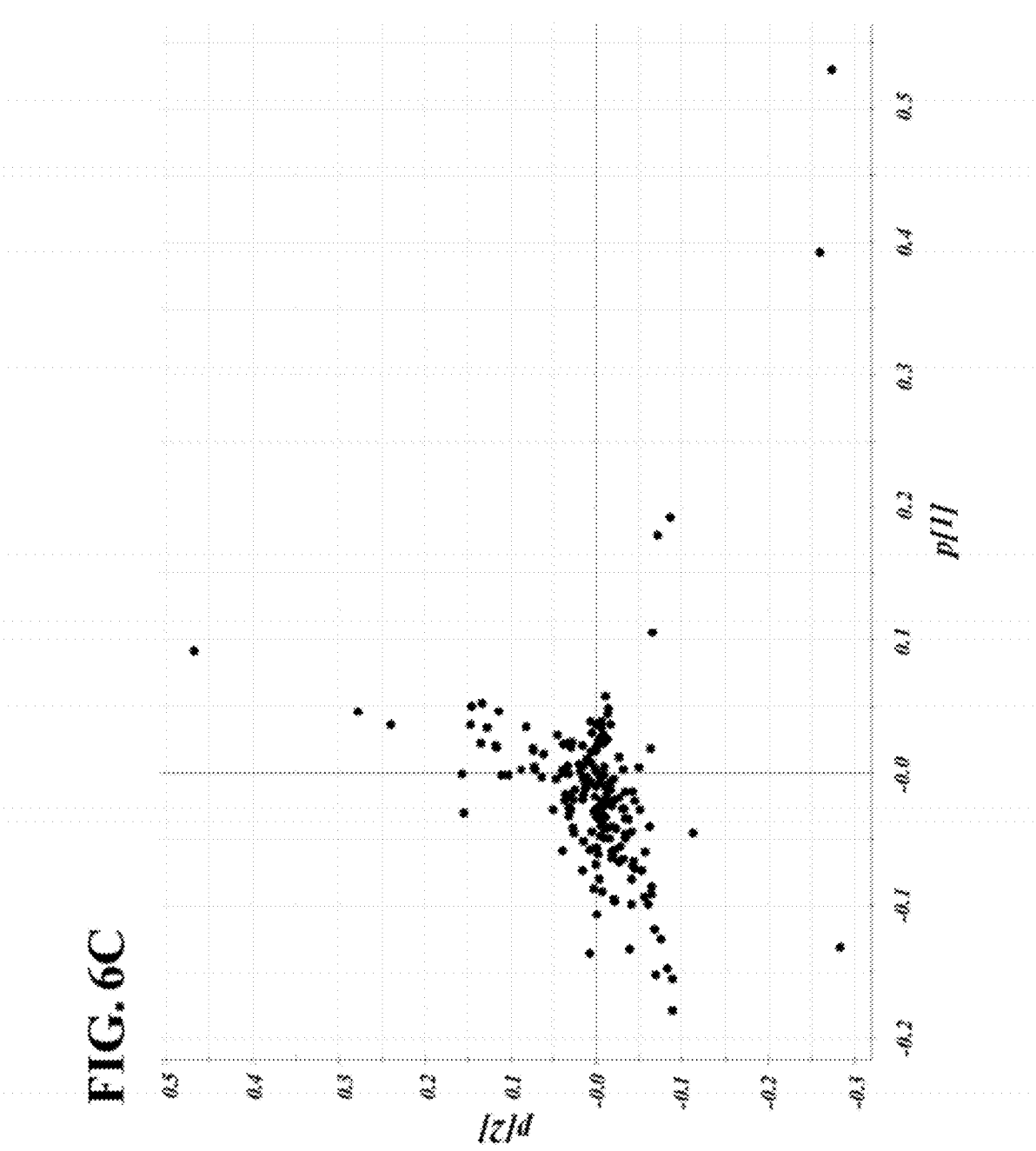

1: increase
2: decrease

FIG. 10

| Groups | WBC (10⁹/L) | %N | %L | %M | %E | %B | RBC (10¹²/L) | Hb (g/dl) | Ht (%) |
|---|---|---|---|---|---|---|---|---|---|
| Sham | 10.0±0.8ᵃ | 7.8±1.5ᵃ | 81.7±2.4ᵃ | 3.1±0.6ᵃ | 5.2±1.0 | 4.2±0.5 | 9.7±0.3ᵃ | 14.9±0.4ᵃ | 51.6±1.3ᵃ |
| Tumor | 8.7±0.7ᵃ | 10.7±2.9ᵃ | 78.0±4.7 | 3.6±1.2ᵃᵇ | 3.9±1.1 | 4.9±1.2ᵃ | 10.3±0.0ᵃ | 15.4±0.1ᵃ | 53.8±0.4ᵃ |
| CP2 | 2.4±0.2ᵇ | 27.3±6.3ᵇ | 66.0±6.4 | 1.2±0.5ᶜ | 2.6±0.1 | 2.0±0.4 | 6.7±0.6 | 10.3±1.1ᵇ | 35.1±4.0ᵇ |
| Pre-DET10 | 7.9±1.4ᵇ | 14.7±2.0ᵇ | 50.2±17.9 | 4.8±0.6ᵇ | 4.0±0.6 | 3.9±0.4 | 8.9±1.4ᵃ | 13.1±2.3ᵃ | 45.8±7.9ᵃ |
| DET10 | 6.8±0.6ᵇ | 18.1±2.5ᵇ | 70.0±3.4 | 3.4±1.1ᵃᵇ | 3.0±0.4 | 4.1±0.4 | 9.3±0.1ᵃ | 13.9±0.1ᵃ | 45.7±2.8ᵃ |
| DET10+CP1 | 4.3±0.7ᵃᵇ | 29.1±9.6ᵇ | 59.4±12.5 | 4.4±0.9ᵇ | 4.4±1.5 | 4.1±1.9ᵃ | 7.1±0.9ᵇ | 11.1±1.6ᵃᵇ | 39.5±5.8ᵃ |
| CP2→DET10 | 4.5±0.8ᵃᵇ | 18.2±6.9ᵇ | 71.5±8.3 | 2.5±0.8ᵃ | 3.2±0.7 | 4.6±0.7 | 8.9±0.5ᵃᵇ | 13.8±0.6ᵃᵇ | 48.9±1.9ᵃᵇ |

| Groups | MCV (fL) | MCH (pg) | MCHC (g/dl) | RDW (%) | PLT (10⁹/L) | MPV (fL) | PCT | PDW (%) | Spleen index (SI) |
|---|---|---|---|---|---|---|---|---|---|
| Sham | 53.3±0.4 | 15.3±0.1 | 28.8±0.2 | 21.1±0.9 | 871.3±16.8ᵃ | 6.4±0.5 | 0.5±0.0 | 19.2±0.2 | 0.36±0.1ᵃ |
| Tumor | 52.6±0.3 | 15.0±0.1 | 28.7±0.2 | 20.6±0.3 | 1052.0±42.6ᵃ | 6.8±0.1 | 0.7±0.0 | 18.2±0.6 | 0.46±0.1ᵃ |
| CP2 | 52.5±1.5 | 15.4±0.3 | 29.4±0.3 | 19.2±3.6 | 548.7±130.5ᵇ | 6.7±0.3 | 0.4±0.2 | 18.0±0.3 | 0.19±0.0 |
| Pre-DET10 | 51.1±0.9 | 14.6±0.3 | 28.5±0.1 | 19.5±0.7 | 1073.0±72.5ᵃ | 7.2±0.7 | 0.7±0.1 | 18.5±0.5 | 0.46±0.2ᵃ |
| DET10 | 52.1±0.5 | 14.5±0.3 | 28.3±0.2 | 20.0±0.4 | 962.7±48.2ᵃ | 6.2±0.1 | 0.6±0.0 | 19.1±0.0 | 0.34±0.1ᵃ |
| DET10+CP1 | 55.5±1.1 | 15.8±0.4 | 28.5±0.2 | 23.3±2.5 | 343.0±116.2ᵃ | 7.3±0.2 | 0.3±0.2 | 20.7±0.8 | 0.50±0.2ᵃ |
| CP2→DET10 | 55.4±1.1 | 15.6±0.2 | 28.2±0.1 | 24.0±0.9 | 666.0±119.1ᵃ | 6.9±0.3 | 0.5±0.1 | 18.4±0.5 | 0.47±0.0ᵃᵇ |

FIG. 11

| Metabolites | Sham control | Tumor | CP2 | pre-IDET10 | IDET10 | IDET10+CP1 | CP2+IDET10 |
|---|---|---|---|---|---|---|---|
| Alanine | 0.40 ± 0.04 | 0.39 ± 0.04 | 0.21 ± 0.03 | 0.39 ± 0.03 | 0.27 ± 0.08 | 0.33 ± 0.05 | 0.28 ± 0.02 |
| Aspartate | 1.44 ± 0.06 | 1.73 ± 0.11 | 0.69 ± 0.04 | 1.82 ± 0.08 | 1.24 ± 0.33 | 1.24 ± 0.12 | 1.24 ± 0.08 |
| Glutamate | 5.07 ± 0.28 | 5.42 ± 0.11 | 4.10 ± 0.34 | 6.42 ± 0.25 | 4.54 ± 1.32 | 5.38 ± 0.77 | 4.40 ± 0.27 |
| Histidine | 0.26 ± 0.04 | 0.33 ± 0.02 | 0.36 ± 0.05 | 0.48 ± 0.09 | 0.35 ± 0.04 | 0.29 ± 0.00 | 0.23 ± 0.02 |
| Isoleucine/Leucine | 2.20 ± 0.08 | 2.57 ± 0.22 | 2.14 ± 0.07 | 2.93 ± 0.76 | 2.73 ± 0.39 | 2.09 ± 0.03 | 2.17 ± 0.23 |
| Methionine | 0.77 ± 0.08 | 0.71 ± 0.06 | 0.57 ± 0.05 | 1.06 ± 0.23 | 0.61 ± 0.13 | 0.50 ± 0.33 | 0.64 ± 0.06 |
| Phenylalanine | 5.71 ± 0.79 | 5.94 ± 0.35 | 3.35 ± 0.19 | 6.14 ± 1.09 | 4.44 ± 0.42 | 5.02 ± 0.56 | 4.28 ± 0.15 |
| Proline | 0.17 ± 0.01 | 0.15 ± 0.01 | 0.15 ± 0.02 | 0.23 ± 0.03 | 0.15 ± 0.06 | 0.17 ± 0.03 | 0.12 ± 0.01 |
| Tryptophan | 8.29 ± 1.01 | 9.59 ± 0.76 | 3.43 ± 0.18 | 9.90 ± 1.87 | 7.27 ± 1.03 | 8.75 ± 0.93 | 6.70 ± 1.12 |
| Valine | 0.60 ± 0.06 | 0.64 ± 0.03 | 0.37 ± 0.03 | 0.85 ± 0.19 | 0.49 ± 0.15 | 0.33 ± 0.05 | 0.40 ± 0.08 |
| Pyruvate | 0.14 ± 0.01 | 0.12 ± 0.03 | 0.22 ± 0.02 | 0.23 ± 0.05 | 0.15 ± 0.01 | 0.15 ± 0.02 | 0.13 ± 0.02 |
| Citrulline | 0.20 ± 0.03 | 0.18 ± 0.10 | 0.50 ± 0.17 | 0.27 ± 0.04 | 0.20 ± 0.10 | 0.29 ± 0.07 | 0.26 ± 0.06 |
| Creatine | 16.96 ± 2.38 | 9.28 ± 3.66 | 26.79 ± 10.15 | 15.22 ± 2.78 | 67.05 ± 46.29 | 16.04 ± 2.85 | 21.55 ± 6.73 |
| Dodecanoic acid | 3.95 ± 0.66 | 6.15 ± 0.66 | 5.47 ± 0.51 | 3.91 ± 0.58 | 4.18 ± 0.42 | 5.50 ± 0.98 | 3.46 ± 0.57 |
| Uric acid | 0.50 ± 0.13 | 1.00 ± 0.44 | 4.19 ± 2.59 | 1.39 ± 0.73 | 1.74 ± 0.67 | 2.30 ± 0.34 | 2.61 ± 1.21 |
| Hippuric acid | 0.42 ± 0.25 | 0.58 ± 0.16 | 5.25 ± 1.24 | 0.32 ± 0.20 | 0.42 ± 0.16 | 1.22 ± 0.6 | 0.56 ± 0.28 |
| Palmitic acid | 1443.11 ± 96.44 | 1416.78 ± 90.59 | 1346.72 ± 114.54 | 1676.80 ± 40.04 | 1495.47 ± 54.82 | 1628.82 ± 81.84 | 1547.60 ± 75.61 |
| Stearic acid | 448.81 ± 38.29 | 444.29 ± 26.59 | 444.87 ± 30.52 | 476.87 ± 49.81 | 468.19 ± 11.92 | 510.29 ± 12.78 | 432.66 ± 45.49 |
| Oleic acid | 79.18 ± 7.5 | 103.72 ± 19.47 | 88.59 ± 8.17 | 95.90 ± 8.18 | 92.60 ± 8.37 | 99.12 ± 6.41 | 79.09 ± 3.14 |
| 5-HIAA | 0.05 ± 0.05 | 0.80 ± 0.00 | 0.43 ± 0.04 | 0.00 ± 0.00 | 0.00 ± 0.00 | 0.30 ± 0.09 | 0.24 ± 0.04 |
| Carnitine | 20.50 ± 1.24 | 16.60 ± 4.62 | 15.89 ± 3.50 | 18.51 ± 1.61 | 46.07 ± 22.03 | 17.91 ± 1.29 | 29.12 ± 4.77 |
| Nicotinamide | 169.25 ± 4.35 | 165.41 ± 12.59 | 119.87 ± 11.72 | 108.18 ± 44.57 | 204.79 ± 59.86 | 163.36 ± 10.84 | 176.93 ± 23.66 |
| Uridine | 0.61 ± 0.04 | 0.41 ± 0.19 | 1.05 ± 0.38 | 0.92 ± 0.15 | 0.91 ± 0.30 | 0.94 ± 0.14 | 1.00 ± 0.23 |
| Myoinositol | 0.59 ± 0.04 | 0.71 ± 0.04 | 0.77 ± 0.09 | 0.77 ± 0.09 | 0.62 ± 0.22 | 0.67 ± 0.09 | 0.76 ± 0.07 |
| L-lactate | 6.02 ± 0.29 | 6.50 ± 0.40 | 6.23 ± 0.12 | 6.35 ± 0.29 | 6.86 ± 1.08 | 6.50 ± 0.22 | 5.16 ± 0.23 |
| Taurine | 4.68 ± 0.55 | 5.71 ± 0.27 | 4.92 ± 0.59 | 7.14 ± 1.17 | 9.67 ± 2.37 | 8.16 ± 0.59 | 4.60 ± 0.06 |

USE OF DEOXYELEPHANTOPIN (DET) AND ANALOGUES THEREOF FOR TREATMENT OF MELANOMA

REFERENCE TO RELATED APPLICATION

The present application claims the priority to U.S. Provisional Application Ser. No. 61/375,538, filed Aug. 20, 2010, which is herein incorporated by reference in its entirety.

FIELD OF THE INVENTION

The present invention relates generally to phytocompounds, and more specifically to use of phytocompounds for treatment of melanoma.

BACKGROUND OF THE INVENTION

Botanicals have been used for treatment of various human diseases throughout history and they play a role in disease prevention. Natural occurring agents, e.g., curcumin and resveratrol possess chemopreventive characteristics such as anti-inflammatory, cell-cycle modulator, antiangiogenic and antimetastatic activities that are in current ongoing clinical trials for various cancers. *Elephantopus scaber* L. is a traditional medicinal plant, which has been claimed for anti-cancer effects. Scientific reports have showed germacranolide sesquiterpene lactones (SLs), such as isodeoxyelephantopin, identified from the plant possesses anti-leukemia KBM-5 cell activity through potentiating tumor necrosis factor (TNF-$\alpha$) mediated apoptosis. Deoxyelephantopin (DET), another SL from *Elephantopus* plant inhibited HeLa cell activity in vivo. Very recently, we demonstrated that DET possesses potent activity against mammary tumor growth and metastasis in syngeneic mice. Moreover, DET exhibits a more profound effect than paclitaxel on survival rate of mammary tumor-bearing mice; however, whether DET is efficacious for melanoma is unknown.

Melanoma is the most lethal form of skin cancer and an increasingly common cancerous disease worldwide. Despite recent advances, the outcomes of chemotherapy for patients with metastatic melanoma are remained unsatisfactory because of the relative drug resistance of metastatic cells and the low survival rates of cancer patients. Besides, chemotherapeutic drugs are usually cytotoxic with strong side effects. Cisplatin (cis-diamminedichloroplatinum(II), CP) is a first line chemotherapy drug, effective in the treatment of a wide variety of neoplastic diseases, such as ovarian cancer, head and neck cancer, testicular cancer, lung cancer, melanoma, etc. Unfortunately, it is also known that CP caused many adverse drug reactions, e.g., renal toxicity, gastrointestinal dysfunction, and peripheral nerve damage in cancer patients. It is estimated that the development of 30% of new drug candidates is halted because of unforeseen toxicity profiles and side effects in clinical studies. The pressing need for development of new therapeutic or preventive agents for melanoma has spurred the search for bioactive phytocompounds with novel modes of action or little side effects.

Therefore, a previously unaddressed need exists in the art to address the aforementioned deficiencies and inadequacies, especially in connection with development of antimelanoma phytocompounds with little side effects.

SUMMARY OF THE INVENTION

In one aspect, the invention relates to a method of treating melanoma in a subject in need thereof. The method comprises administering to the subject a composition comprising: a) a therapeutically effective amount of deoxyelephantopin and/or an analogue thereof; and b) a pharmaceutically acceptable carrier.

In another aspect, the invention relates to a method of inhibiting proliferation, migration and/or metastasis of melanoma cells in a subject in need thereof. The method comprises administering to the subject a composition comprising: a) a therapeutically effective amount of deoxyelephantopin and/or an analogue thereof; and b) a pharmaceutically acceptable carrier.

Further in another aspect, the invention relates to a method of preventing and/or reducing side effects of an anti-cancer agent in a subject in need thereof. The method comprises administering to the subject a composition comprising: a) a therapeutically effective amount of deoxyelephantopin and/or an analogue thereof; and b) a pharmaceutically acceptable carrier.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 1 shows Anti-B16 melanoma cell proliferation effects by DET and cisplatin. A, Chemical structures of DET, DET analogues, and cisplatin. B1-B2, Human melanocyte and B16 melanoma cells were treated with the indicated concentrations of DET or cisplatin at 37° C. for 24 h. Cell viability (%) was determined by MTT assay. C1, Isobologram of DET and cisplatin interaction. Combination index was determined using isobologram analysis at IC50. The value of CI<1 indicates synergism. The dashed line indicates the zero interaction of the isobole. C2, A Fa vs. CI plot of DET and cisplatin combinational treatment. Data are mean±SD of three separated experiments.

FIG. 3 shows DET inhibited metastasis of B16 melanoma cells. A1-A2, Wound healing and invasion analysis. B1, MMP-9, MMP-2 protein expression by immunoblotting. B2, MMP-9 activity by zymography. C1-C3, Kinetic characteristics of B16 cell motility with DET or CP treatment. C1, Individual trajectories of B16 cells displayed in diagrams drown with the initial point of each trajectory placed at the origin of the plot. C2, Cell motility was assessed by time-lapse videomicroscopy. C3, Average of the migration velocities and distance of B16 melanoma cells treated with DET or CP within 24 h. Data are mean±SD of three independent experiments.

FIG. 4 shows the effect of DET and cisplatin treatment on suppression of lung metastasis in C57BL/6J mice using in vivo luminescence imaging system (A1, Day 21; C1, Day 30).

A2 and C2, Bioluminescence intensities in each treatment groups were measured weekly and are presented as growth curves. The intensity of luminescence images depicts the antitumor effects of compound or drug in test mice. Data are mean±SEM (n=6) ($P<0.05$). B1, Lung sections of mice from each groups stained with haemotoxylin and eosin (200× original magnification). B2, Bar graphs depicting the relative weight of lung to body in test mice. D1, Effect of DET and cisplatin on the survival rate. D2, Effect of DET and cisplatin on mean body weight as a function of days of treatment in C57BL/6J mice carrying metastatic B16 melanoma tumors ($P<0.05$).

FIG. 5 shows histopathological examination of kidney tissues of control and tumor-bearing mice treated with DET, cisplatin, or combinational treatment of DET and cisplatin. A, Kidney sections of mice from each groups stained with haemotoxylin and eosin (200× original magnification). B, Apoptosis cells determined by TUNEL assay. A representative image of each treatment group is shown. C1, TUNEL-positive cells in calculated by number of positive (brownish) cells. Levels of blood urea nitrogen (BUN) in mice with various treatments. C2, The plasma BUN in mice were determined at 1, 2 and 3 weeks after compound/drug administration in C57BL/6J mice (n=3). Values are means±SD ($P <0.05$). D1, D2, Positive stained of F4/80 mMacrophage/monocyte infiltration stained by F4/80 was visualized at 200× magnification by use of a Nikon fluorescent microscope. Bar graphs depicting the F4/80 total intensity of kidney tissues in test mice. Values are means±SD ($P<0.05$).

Figure 6D:
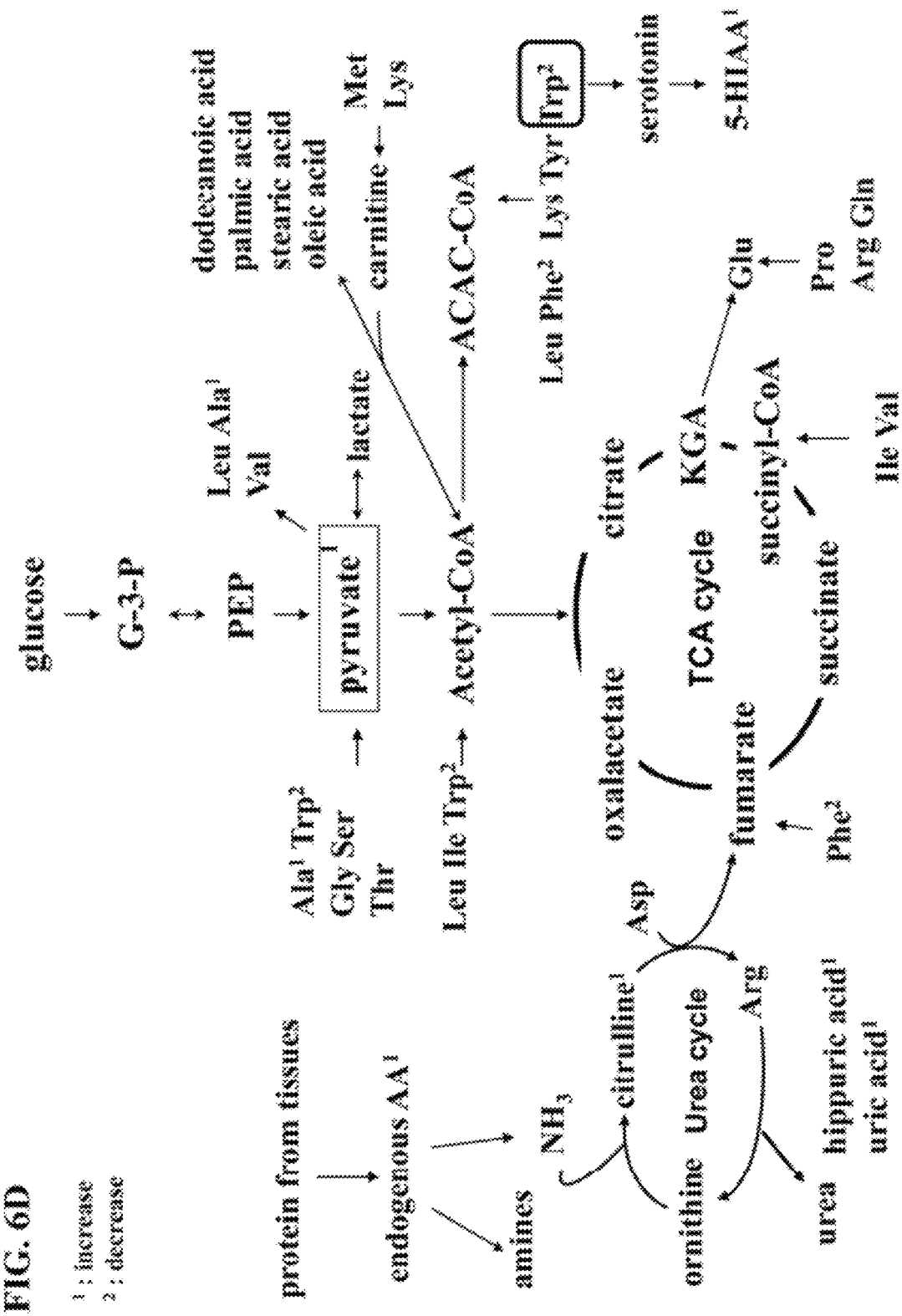

FIG. 6 shows score plots for DET, CP or combinational treatment of DET and CP based on covariances of the NMR data. A, The peaks are labeled according to their chromatographic retention times and m/z values. B-C, The score plot for kidney profiling and corresponding loadings plot for kidney profiling for PCA of UPLC-QTOF mass data derived from all mice. The scores plot shows distinct clustering of the treatment groups. The loadings plot represents the impact of the metabolites on the clustering results. The ions most responsible for the variance in the scores plot are indicated on the loadings plot by their distance from the origin. D, Hypothetical mechanism of cisplatin induced kidney toxicity in mice generated based on the finding from metabolomics. Affected amino acid and endogenous metabolites are indicated in the appropriate biological pathway involved.

Figure 7:
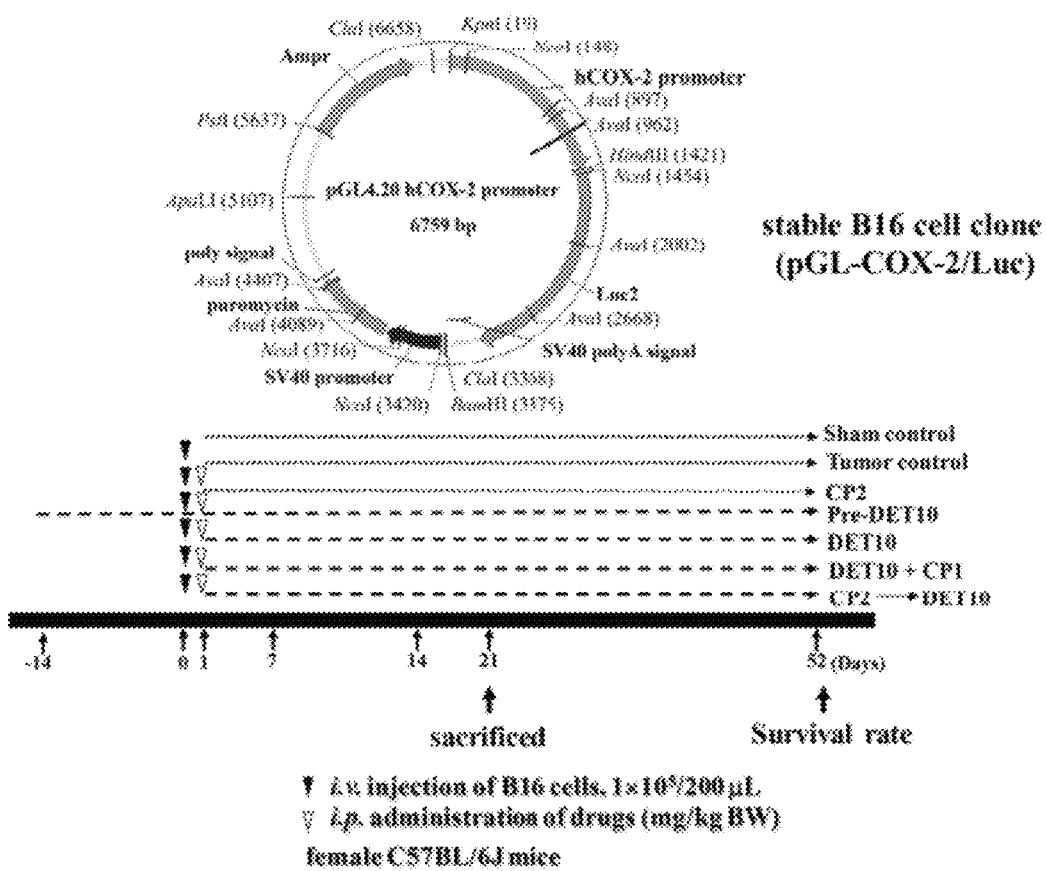

FIG. 7 shows a summary of experimental design for the study of preventive and therapeutic effects of DET, cisplatin on metastatic B16 melanoma.

Figure 8:
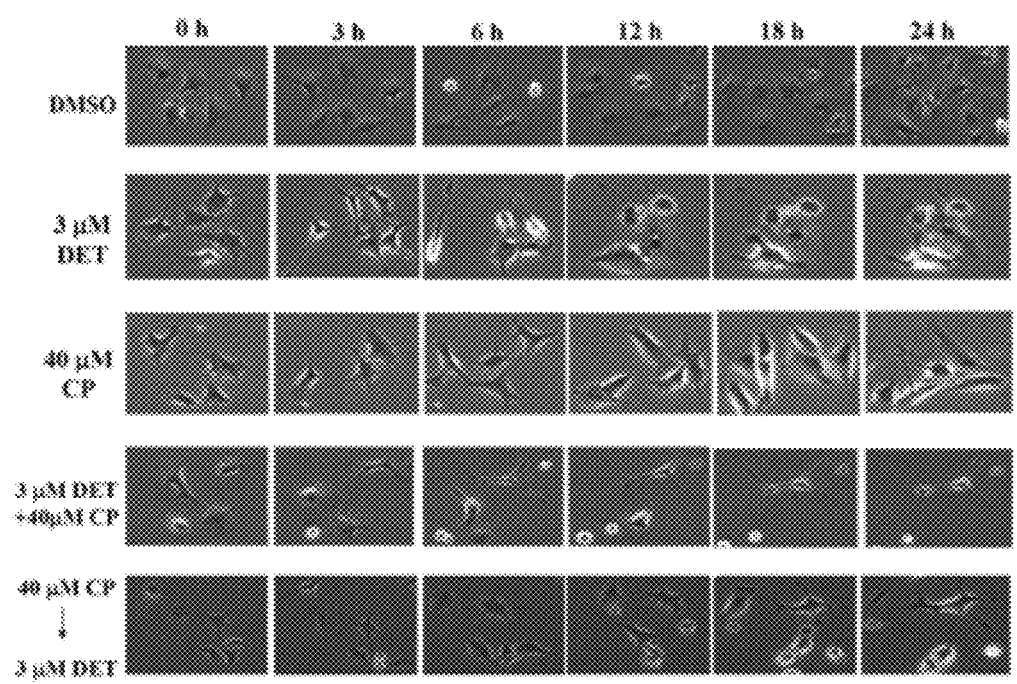

FIG. 8 shows time-lapse images of B16 cell motility with DET or cisplatin treatment.

Figure 9:
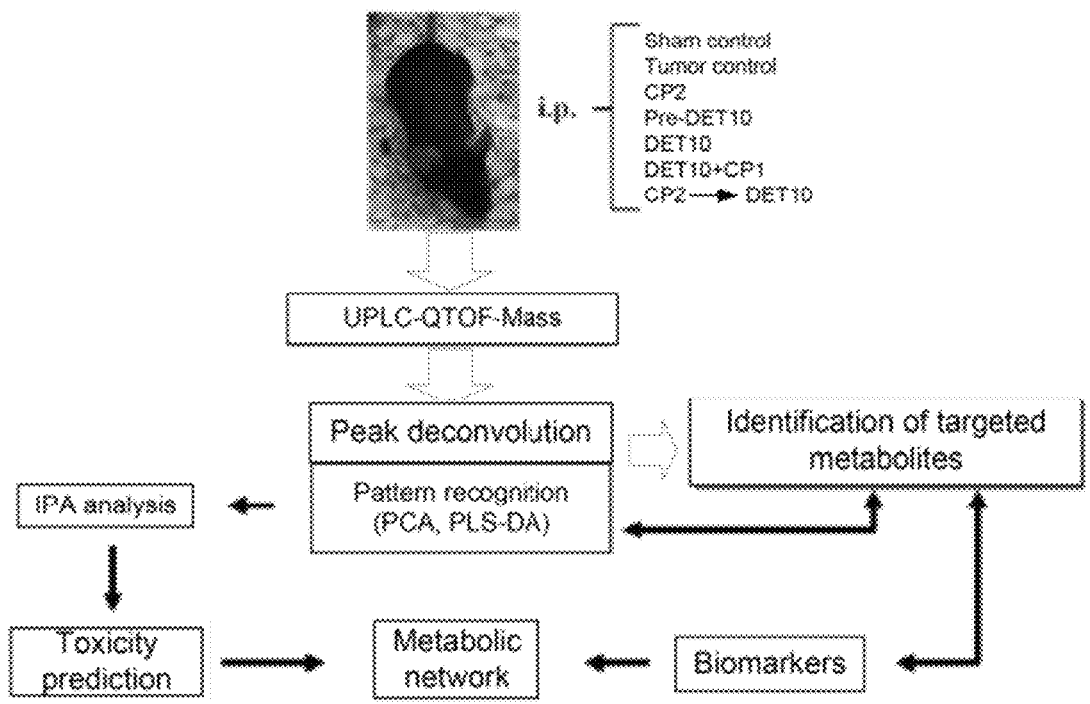

FIG. 9 is a schematic representation of the workflow for evaluations of cisplatin and DET system toxicity.

FIG. 10 is a table showing the effect of DET or cisplantin treatment on the peripheral blood cell profile of B16 melanoma-bearing mice.

FIG. 11 is a table showing metabolite profiles of kidney tissues in test mice with different treatments.

DETAILED DESCRIPTION OF THE INVENTION

The present invention is more particularly described in the following examples that are intended as illustrative only since numerous modifications and variations therein will be apparent to those skilled in the art. Various embodiments of the invention are now described in detail. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "treating" or "treatment" refers to administration of an effective amount of the compound to a subject in need thereof, who has cancer, or a symptom or predisposition toward such a disease, with the purpose of cure, alleviate, relieve, remedy, ameliorate, or prevent the disease, the symptoms of it, or the predisposition towards it. Such a subject can be identified by a health care professional based on results from any suitable diagnostic method.

"An effective amount" refers to the amount of an active compound that is required to confer a therapeutic effect on the treated subject. Effective doses will vary, as recognized by those skilled in the art, depending on rout of administration, excipient wage, and the possibility of co-usage with other therapeutic treatment.

The term "an analogue" means one of a group of chemical compounds similar in structure but different in respect to elemental composition. An analogue of deoxyelephantopin (DET) is a phytocompound having analogy to DET. The term "analogy" means similarity.

The term "orthotopic melanoma" means the primary tumor before metastasis stage which will be basically in skin.

The discovery disclosed here relates to the efficacy of deoxyelephantopin (DET), a major sesquiterpene lactone constituent of *Elephantopus scaber* L. (Asteraceae), against B16 melanoma cell activity and metastasis, in parallel compared with that of chemotherapeutic drug cisplatin (CP). DET and cisplatin inhibited B16 cell proliferation with IC50 value at 4.5 µM and 45 µM, respectively. Isobologram analysis further revealed the synergism of DET and cisplatin against B16 cell proliferation. A series of drug treatment protocol were designed in this study, i.e., DET or CP treatment alone, DET co-treated with CP (DET+CP), and sequential treatment with CP then DET (CP→DET). A non-invasive real-time in vivo imaging system to monitor the melanoma cell growth and metastasis in syngeneic C57BL/6J mice was established by using stable B16 melanoma cell clone carrying COX-2 promoter driven-luciferase reporter gene. It was found that Pre-DET10 (10 mg/kg BW) and cisplatin (CP, 2 mg/kg BW) have similar profound effect in inhibiting lung metastasis of B16 melanoma and increasing median survival rate in tested mice. Cisplatin resulted in renal damages and haematological toxicity in mice that were not seen in DET10 treatment group, moreover, DET and CP cotreatment showed little or no side-effects. Metabolomic study on kidney tissues using ultra performance liquid chromatography (UPLC)-QTOF mass spectrometry delineated the cisplatin-induced nephrotoxicity that was not seen in tumor-bearing mice treated with DET alone or DET combined with cisplatin. DET could induce cell cycle arrest at G2/M phase, with the decrease of cyclins A, B1, and D1 protein expression, and activation of apoptotic hallmarks PARP and caspase-3. It was found that DET could reduce or recover the side effect of cisplatin in melanoma-bearing mice. The findings may prove useful in further explorations of the application of these combinational approaches to the treatment of malignant melanoma.

The extract of *Elephantopus scaber* contains DET and at least three other forms of DET analogs. The DET analogs are predicted to have similar bioactivity. Both DET and IDET inhibited breast cancer cell activity and similarly effective.

Metabolomics is an emerging science and technology system by comprehensive experimental analysis of metabolite profiles, either as a targeted subset of related chemicals or more globally, for diverse applications in diagnosis, toxicology, disease development, genetic modification of specific organisms, drug discovery and development, and phytomedicines. The effects of DET alone and DET sensitizing cisplatin were investigated in a designed co- or sequential treatment strategy, against B16 cell activity in vitro and B16 cell metastasis in syngeneic C57BL/6J mouse. Metabolomics approach was used to evaluate the DET effect on attenuating cisplatin-induced renal damage in tumor bearing mice.

In one aspect, the invention relates to a method of treating melanoma in a subject in need thereof. The method comprises administering to the subject a composition comprising: a) a therapeutically effective amount of deoxyelephantopin and/or an analogue thereof; and b) a pharmaceutically acceptable carrier.

In one embodiment of the invention, the method further comprises administering to the subject at least one additional anti-melanoma agent in a therapeutically effective amount.

In another embodiment of the invention, deoxyelephantopin and/or the analogue thereof and the at least one additional anti-melanoma agent are administered sequentially or simultaneously.

In another embodiment of the invention, the at least one anti-melanoma agent is chosen from cisplatin, betulinic acid, 4-S-cysteaminyl catechol, 4-S-cysteaminyl phenol, everolimus, bortezomib, paclitaxel, carboplatin, dacarbazine, celecoxib, temozolomide, sorafenib, thalidomide, lenalidomide, oxaliplatin, docetaxel, valproic acid, vinblastine, imatinib mesylate, bosentan, doxorubicin, apomine, arsenic trioxide, carmustine, vinblastine and tamoxifen.

In another embodiment of the invention, deoxyelephantopin and/or the analogue thereof is administered to the subject after cisplatin.

In another embodiment of the invention, the composition further comprises at least one additional anti-melanoma agent in a therapeutically effective amount.

In another embodiment of the invention, the composition comprises an extract of *Elephantopus scaber* L., the extract comprising the therapeutically effective amount of deoxyelephantopin and/or the analogue thereof.

Further in another embodiment of the invention, the analogue is chosen from isodeoxyelephantopin, scabertopin, isoscabertopin, and any combination thereof.

In another aspect, the invention relates to a method of inhibiting proliferation, migration and/or metastasis of melanoma cells in a subject in need thereof. The method comprises administering to the subject a composition comprising: a) a therapeutically effective amount of deoxyelephantopin and/or an analogue thereof; and b) a pharmaceutically acceptable carrier.

Further in another aspect, the invention relates to a method of preventing and/or reducing side effects of an anti-cancer agent in a subject in need thereof. The method comprises administering to the subject a composition comprising: a) a therapeutically effective amount of deoxyelephantopin and/or an analogue thereof; and b) a pharmaceutically acceptable carrier.

In one embodiment of the invention, the anti-cancer agent comprises cisplatin.

In another embodiment of the invention, the anti-cancer agent comprises at least one anti-melanoma agent other than deoxyelephantopin or the analogue thereof.

Further in another embodiment of the invention, the therapeutically effective amount of deoxyelephantopin and/or the analogue thereof and the anti-cancer agent is sequentially or simultaneously administered to the subject.

Yet in another embodiment of the invention, the side effects are chosen from kidney damage, haematological toxicity, a loss of body weight, and any combination thereof.

Further in another aspect, the invention relates to a dietary supplementary composition comprising deoxyelephantopin and/or an analogues thereof.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods

Materials

Minimum essential medium (MEM), RPMI medium 1640 (Gibco/BRL), fetal bovine serum (FBS), penicillin, streptomycin, Lipofectamine PLUS were obtained from Invitrogen. 3-(4,5-Dimethylthiazol-2-yl]-2,5-diphenylterazolium bromide salt (MTT), RNase A, propidium iodide, puromycin, D-luciferin, formaldehyde, dimethyl sulphoxide (DMSO) and cisplatin (cis-diamminedichloroplatinum(II), CP), 4',6- diamidino-2-phenylindole (DAPI), gelatin, polyacrylamide, Triton X-100 and Coomassie blue R250 were obtained from Sigma Chemical (St. Louis, Mo.). P-p53, p53, p21, p27, cdk1, cyclinA, cyclin B1, Bax, Bid, GSK-3β and cyclin D1 were from Santa Cruz Biotechnology (Santa Cruz, Calif.) and PARP, caspase-3, p-AKT, AKT and p-GSK-3β were from Cell signaling Technology (Danvers, Mass.). Chemiluminescence reagents was obtained from Amersham (Arlington Heights, Ill.). Matrigel basement membrane matrix was obtained from BD Biosciences (San Jose, Calif.). TUNEL assay kit was obtained from Chemicon. F4/80 (pan-macrophage marker) was obtained from e-Bioscience company. Other chemicals were of reagent grade.

Isolation of DET

Deoxyelephantopin was isolated from a medicinal plant *Elephantopus scaber* L. (Asteraceae) followed the method we published previously (Huang et al. (2010) "Deoxyelephantopin, a novel multifunctional agent, suppresses mammary tumor growth and lung metastasis and doubles survival time in mice" *Br J Pharmacol* 159:856-71, which is incorporated herein by reference in its entirety). The structure of DET was elucidated by electrospray ionization mass spectrometry (Thermo Finnigan LCQ, San Jose, Calif.), $^1$H and $^{13}$C NMR spectrometry (Brüker ADVANCE 500 AV) and confirmed by comparison of the spectral data with previously published results (ibid; But et al (1997) "Sesquiterpene lactones from *Elephantopus scaber*" *Phytochemistry* 44:113-6). The purity of DET was >97% as evident by HPLC/mass analysis.

Cell Culture and Cell Viability Assay

Human melanocytes and murine B16 melanoma cells obtained from the American Type Culture Collection (ATCC®, MD) were grown overnight in a 10-mm petri-dish at 37° C. in MEM and RPMI medium 1640, respectively, supplemented with 10% heat-inactivated FBS, 100 units/mL penicillin, and 100 μg/mL streptomycin, in a humidified 5% $CO_2$ incubator. Cell viability was measured by MTT-based colorimetric assay. The formula to calculate viable cell (%) is as follows:

Cell viability (%)=(sample $OD_{550}$/control $OD_{550}$)× 100%

Synergism of DET and Cisplatin

Synergistic effects of DET and CP (Cis-Diammineplatinum(II)dichloride, cisplatin, Sigma) were determined with fixed concentrations of DET ranging from 0.5 to 3 μM and cisplatin from 5 to 50 μM. Briefly, cells ($5\times10^3$ cells/well) were seeded in 96-well plates and treated with DET and cisplatin alone or in combination for 24 h. Cell proliferation was measured by MTT assay. Chou-Talalay method and isobologram analysis were used to determine the effects of compound drug combinations on B16 cells. The interaction of two compounds was determined by the combination index (CI), and the CI plot was generated using CompuSyn software. The combined effects of the two compounds can be categorized as follows: CI=1 indicates additive and a interaction; CI<1 indicates synergism, and CI>1 indicates antagonism.

Drug Treatment

For in vitro study in the present report, B16 cells were treated with vehicle (0.1% DMSO), 45 μM CP, 5 μM DET, or 3 μM DET plus 40 μM cisplatin combination treatment at indicated times.

Time-lapse Cell Motility Assay

Cell motility was assessed by time-lapse videomicroscopy. B16 cells were seeded in 6 cm dish for 3 h and maintained at constant temperature (37° C.) and 5% $CO_2$ chamber throughout the experimental period. Cells were observed under an inverted microscope (Zeiss Axiovert 200M), and phase-contrast snap photographs (one frame every 30 min) were digitally recorded for 24 h. Cell paths were generated from centroid positions, and cell velocities of migration were analyzed using the tracking object of the Metamorph software (Molecular Device).

Migration and Invasion Assay

B16 cells ($1\times10^5$ cells) were cultured in culture-inserts of boyden chamber (ibidi, Germany) for 12 h. The culture-inserts were removed and added DET or cisplatin alone or in combination for 24 h. B16 cells were added into a 24-transwell permeable plate (8.0 μm polycarbonate membrane, 6.5 mm insert; Corning Incorporated, Corning, N.Y.) coated with Matrigel basement membrane matrix. The bottom wells received 50 μL medium having the same concentration of serum as the top well, either 1% or 10% FBS. Cells were removed from the upper and lower sides of the filter after 24 h. The ratio of the counts obtained from the bottom versus total counts from both sides was used to determine migration and invasiveness. The invading cells remaining in the well were counted in six randomly chosen low-power fields at 100× original magnification by inverted fluorescence microscopy.

Cell Cycle Analysis

Cell cycle analysis was carried out as previously described (Shyur et al. (2004) "Induction of apoptosis in MCF-7 human breast cancer cells by phytochemicals from *Anoectochilus formosanus*" *J Biomed Sci;* 11:928-39 (19)). B16 cells ($5\times10^5$) were synchronized by incubation in medium containing 1% FBS for 12 h and the culture was then incubated with fresh medium/10% FBS containing vehicle, cisplatin, DET, or DET+CP for 24 h. Both adherent and floating cells were collected, washed with PBS and fixed with 1 mL of ice-cold 70% ethanol overnight at 4° C. Cells were stained with 0.2 mg/mL RNase A and 0.02 mg/mL propidium iodide in darkness for 30 min at room temperature and analyzed on flow cytometry (Flow cytometer BD LSR II).

Western Blotting

Total cellular proteins were prepared from test cells according to Chiang et al (2005) ("Ethyl caffeate suppresses NF-κB activation and its downstream inflammatory mediators, iNOS, COX-2, and PGE2 in vitro or in mouse skin" *Br J Pharmacol* 146:352-63). Protein concentration was determined by Bradford method (Bio-Rad Laboratories, Hercules, Calif.). Thirty μg protein sample in each lane was resolved by 5-20% gradient mini-SDS-PAGE and subjected to western blotting against selected antibodies at 4° C. overnight, and proteins for specific reacted bands were resolved by use of enhanced chemiluminescence reagents.

MMP-2 and MMP-9 Activity Assay

Analysis of gelatin zymography of MMP-2 and MMP-9 activities was performed according to the method previously described (Snoek-van Beurden et al. (2005) "Zymographic techniques for the analysis of matrix metalloproteinases and their inhibitors. Biotechniques" 38:73-83.). After the treatments, the conditioned media were collected, concentrated and subjected to SDS-PAGE with polyacrylamide gels copolymerized with 0.1% gelatin. Gels were rinsed in washing buffer and incubated overnight at 37° C. in zymogram development buffer. Gels were fixed and stained with filtrated 0.1% Coomassie blue R250. Gelatinolytic activity is visualized as a clear band against a dark background of stained gelatin. MMP-2 and MMP-9 activities were detected by a clear band appearing at 72 and at 92 kDa, respectively.

Transfection and Stable Cell Line Generation

Stable B16 melanoma cell clone carrying COX-2 promoter driven-luciferase (pGL-COX-2/Luc) reporter gene plasmid was established. A gene plasmid was constructed in the pGL4.20-Basic vector containing a luciferase reporter gene driven by the full length 5' flanking promoter region (−1334/−1) of the human COX-2 promoter (Hou et al. (2007) "A galactolipid possesses novel cancer chemopreventive effects by suppressing inflammatory mediators and mouse B16 melanoma. Cancer Res" 67:6907-15) (FIG. 7), which was transfected into B16 melanoma cells using Lipofectamine PLUS (Invitrogen). A stable B16 cell clone (designated B16-COX-2/Luc) carrying the reporter gene and displaying the highest level of luciferase expression and activity among the selected transfected clones was isolated by several passages of antibiotic puromycin (0.5 μg/mL) selection. The B16-COX-2/Luc stable cell line was used in the mouse lung metastasis experiments.

Inhibition of Lung Metastasis of B16 Cells in Syngeneic Mice

Female C57BL/6J mice (National Laboratory Animal Center, Tainan, Taiwan) were given a standard laboratory diet and distilled water ad libitum and kept on a 12-h light/dark cycle at 22±2° C. In total, 63 mice were randomly divided and assigned into 7 groups. A scheme of the experimental design is shown in FIG. 7. Female C57BL/6J mice received an intravenous (i.v) injection with $1 \times 10^5$ B16 cells in 200 μL PBS through the tail vein at Day 0. On Day 1, mice were divided into tumor group, CP2 group, DET10 group, DET10+CP1 group, and CP2→DET10 group. The mice were treated intraperitoneally (i.p.) every two days with 2 mg/kg body weight (BW) cisplatin (CP2), 10 mg/kg BW DET (DET10), DET10 mixed with 1 mg/kg BW cisplatin (DET10+CP1), and with CP2 five times and DET10 five times, then CP2 and DET10 taking turns every two days till the end of the experiments (CP2→DET10 group), respectively. The Pre-DET10 group mice were treated i.p with DET (10 mg/kg BW) every two days two weeks before (Day 14) tumor cells inoculation on Day 0, and continuously treated with DET10 till the end of the experiment. The tumor control mice were treated with vehicle DMSO. The mice in the sham control group were injected i.p. with 20 μL DMSO on Day 1 every 2 days throughout the experimental period. Tumor volumes were measured every 3 days and the body weight recorded once a week. On Day 21 post-tumor injection, three mice from each group were euthanized and blood collected for complete blood count (CBC) analysis. Paraffin-embedded lung tissues with tumor colonized were sectioned for hemotoxylin and eosin (H&E) staining, and tumor colonies in left lungs of test mice was counted. The survival rates of the rest of mice in all test groups were recorded over 52 day period and analyzed by a long rank test.

In vivo Bioluminescence Imaging

Prior to the in viva imaging, mice were anesthetized with isoflurane (USP, South Carolina) in an acrylic chamber with 2.5% isoflurane/air mixture and injected i.p. with substrate D-luciferin solution (150 mg/kg BW) in PBS. After 10 minutes of incubation with luciferin, each mouse was placed in a right lateral decubitus position and a digital grayscale animal image was acquired using an IVIS spectrum (Xenogen Corp.). The acquisition and overlay of a pseudocolor image was taken, which represents the spatial distribution of detected photons emerging from active luciferase within the animals. Signal intensity was quantified using an IVIS Spectrum system (Xenogen Corp.) as the sum of all detected photons per second on Day 0, 7, 14, 18, 21, 23, 26 and 30 of treatment.

Histological Examination and Immunohistochemistry Staining of Kidney Tissues

Paraffin-embedded kidney tissues were prepared from three mice in each group on Day 21. The paraffin-embedded kidney was sectioned (4 μm) and underwent H&E staining. In situ apoptotic cells in kidney tissues were determined by TUNEL assay (Chemicon) and the mean proportions of positive TUNEL cells were measured using AxioVision software (Carl Zeiss MicroImaging, Inc.). Immunostaining of macrophage infiltration in the kidney tissues was performed using F4/80 antibody and visualized with goat anti-mouse Cy3-labeled secondary antibodies (Jackson ImmunoResearch), counterstained with DAPI (1 μg/mL).

Ultra Performance Liquid Chromatography/Electrospray Ionization Q-TOF Mass Spectrometry (UPLC/ESI-Q-TOF MS) and Metabolite Data Processing Primary metabolome in the kidney tissues of test mice with various treatments were analyzed using UPLC-QTOF MS. Kidney samples (150 mg) were homogenized with 600 μL methanol and 127.5 μL distilled water. The homogenates were vigorously mixed with 1.2 mL chloroform:H2O solution (1:1, v/v) and then put at −20° C. for 20 min. After centrifugation at 13000×g for 10 min at 4° C., the supernatant (water layer) was collected, dried in a vacuum, and then reconstituted in 100 μL of 50% methanol for analysis.

LC-MS was performed with a LC system (ACQUITY UPLC, Waters, Millford, Mass.) coupled to a hybrid Q-TOF mass spectrometer (Synapt HDMS, Waters, Manchester, U.K.). The sample was separated online with a reverse-phase column (HSS T3 C18, 1.8 μm, 2.1 mm×150 mm, Waters, Milford, Mass.) which was kept in a column oven at 40° C. The mobile phases for positive ion mode consisted of 0.1% formic acid in 2% ACN (buffer A) and 0.1% formic acid in 100% ACN (buffer B). The mobile phases for negative ion mode consisted of pure H2O (buffer A) and pure 100% AcCN (buffer B). The injection volume was 8 μL and the mobile phase flow rate was 500 μL/min using a 4 min gradient form 5-95% ACN/water.

The mass spectrometer equipped with lock electrospray ionization probe was operated in both positive and negative (ESI) modes. The electrospray voltage was set at 3 kV for positive ion mode and −2.5 kV for negative ion mode, and the cone voltage was 40V. The cone and desolvation gas flow were 50 and 700 L/h, respectively. A lock mass calibration of sulfadimethoxin (0.5 mg/L) in water/MeOH (50:50, v/v) was introduce by the HPLC pump (LC-10ATVP, Shimadzu, Japan) and split the 5 μL/min to the lockspray probe. The acquisition method was set to one full MS scan (50-990 m/z) with 0.2 sec scan time in centroid data mode.

The UPLC-MS data were analyzed using MarkerLynx XS version 4.1 SCN639 (Waters, Millford, Mass.). In this application, the peaks in the 0.5-4 min LC-MS data were detected and the noise reduced in both LC and MS domains. The extracted peak information was also processed to remove the peak-to-peak noise, deisotope and filter the MS peak with the intensity lower than 50 counts. A list of the intensities of the processed peaks for each of the LC-MS data was generated using retention time (RT) and m/z data pairs as the identifier of each peak. The processed data for each sample were combined and aligned for each of the RT-m/z pair to generate the final data table. The ion intensities for each peak were then normalized within each sample and the 3-dimensional data, peak identifier (RT-m/z pair), sample name, and ion intensity were analyzed by principle component analysis (PCA). Partial least-squares-discriminant analysis (PLS-DA), a supervised chemometric procedure, was used to define the maximum classification and separation of independent samples.

Statistical Analysis

All data were expressed as means±SD. For the survival data, the log-rank test was used to determine differences among tumor control, drug and compound treated groups. For other experiments, differences between treatments were determined by ANOVA. A P<0.05 is considered statistically significant.

Results

DET Sensitizes B16 Melanoma Cells to Cisplatin

FIG. 1A shows structures of DET, DET analogues and ciplantin. DET and cisplatin (CP) exhibited dose-dependent inhibition on B16 cell proliferation, with $IC_{50}$ values at 4.5 µM and 45 µM, respectively, as determined using MTT assay (FIGS. 1 B1-B2). Both DET and CP showed little or no toxicity on normal human melanocytes (FIGS. 1 B1-B2). We further determined whether DET shows synergism with CP against B16 melanoma cell proliferation using isobolography method and a combination index (CI) method of Chou-Talalay. The isobol-curve and CI plot (FIGS. 1C1-C2) show typical synergistic effect of compound and drug interaction with CI<1 when measured the 50% inhibition of B16 cell proliferation with a serial of combination treatment by DET and CP.

Kinetic Characteristics of B16 Cell Motility or Migration with DET, Cisplatin or Combinational Treatment It was found that the B16 cells in the vehicle control group were normally proliferative and doubling after a-24 h culturing time, but that was not seen in the DET, CP or DET+CP treated cells, as monitored by time-lapse videomicroscopy (FIG. 8). FIG. 3 shows on trans-well assays that DET, CP or DET+CP inhibited B16 melanoma cell migration (FIG. 3A1) and invasion (FIG. 3A2) partly through inhibition of MMP-9 protein expression (FIG. 3B1) and the enzymatic activity of MMP-9 and MMP-2 (FIG. 3B2). The effects of DET, CP, or DET+CP on cell motility of B16 cells was assessed by time-lapse videomicroscopy by monitoring the individual trajectories of B16 cells (FIG. 3C1), quantified by cells migration velocity (µm/min) and migration distance (µm) (FIGS. 3C2 & C3). FIG. 3C2 shows that the migration velocity in vehicle control, CP, DET, DET+CP and CP→DET were determined at 0.35±0.09; 0.26±0.14; 0.16±0.06; 0.1±0.04; and 0.2±0.09 µm/min respectively, and the migration distance were vehicle control: 488.2±147.1; CP: 376.6±100; DET: 224.1±85.9; DET+CP: 149.7±64.4; CP-+DET: 287.5±131.8 µm. These data demonstrated that 3 µM DET and 3 µM DET plus 40 µM CP exhibited a more potent inhibitory activity than that of the B16 cells treated with 40 µM CP.

Figure 2A:
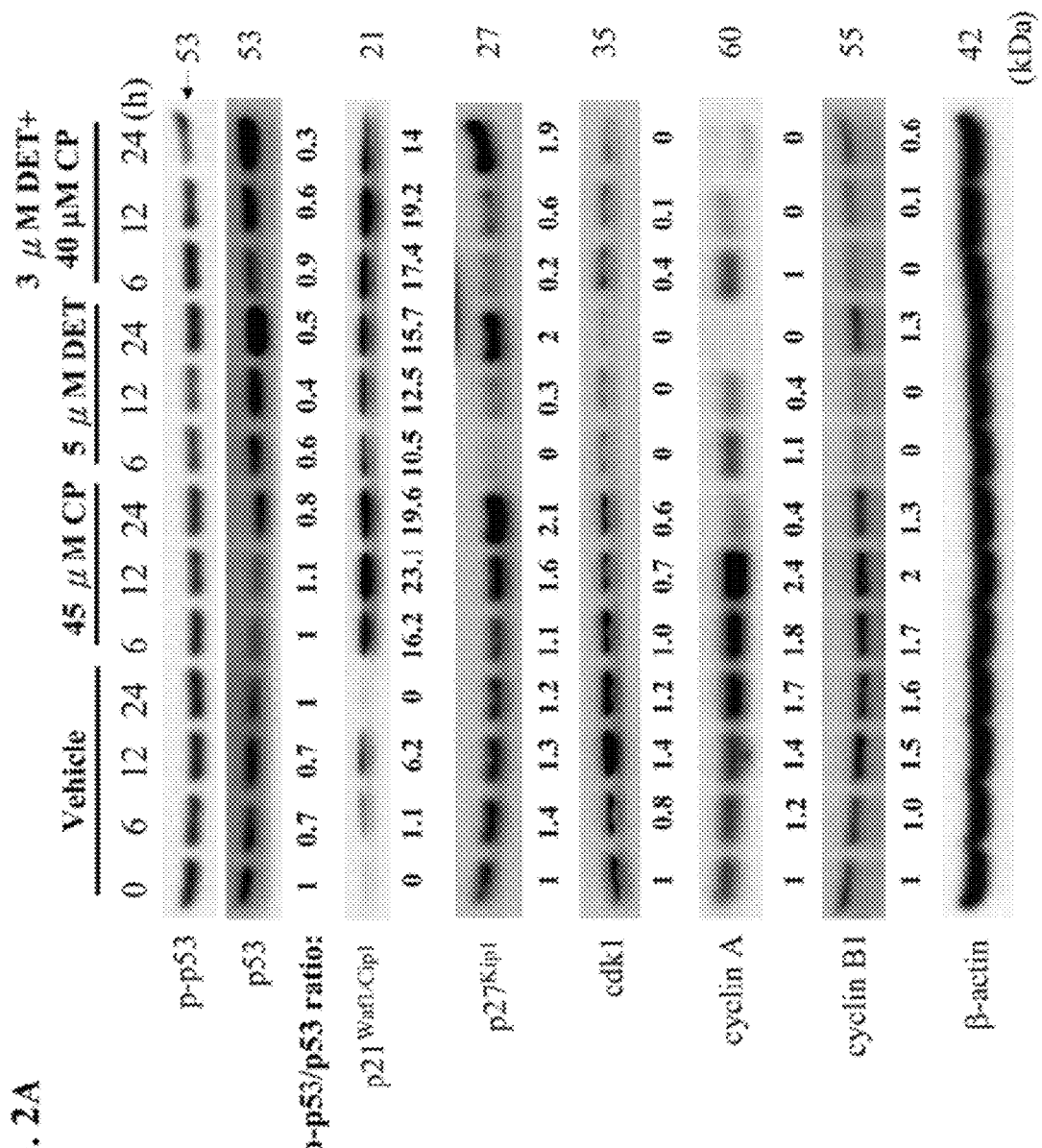
FIG. 2 shows DET and CP induced cell cycle arrest in B16 cells. A, Immunoblotting of key biomarkers involved in G2/M phase mediators. B, AKT and GSK-3$\beta$ protein expression. C, apoptosis pathway in B16 cells. The cell lysates of B16 cells treated with vehicle (0.1% dimethyl sulphoxide, DMSO), 45 $\mu$M cisplatin, 5 $\mu$M DET or 3 $\mu$M DET and 40 $\mu$M cisplatin combination treatment for 6, 12 and 24 h.

DET Regulates Key Biomarkers in the $G_2$/M Cycle Transition and in Apoptosis of B16 Cell In FACScan analysis, this suppression of proliferation was due to DET and cisplatin-induced cell-cycle arrest at $G_2$/M phase in B16 melanoma cells (data not show). Increased expression of $p21^{Waf1/Cip1}$ is indicative of p53 activation in response to DNA damage. Moreover, the western blot data also showed that cisplatin treatment increase $p21^{Waf1/Cip1}$ expression in B16 melamona cells (FIG. 2A).

Figure 2B:
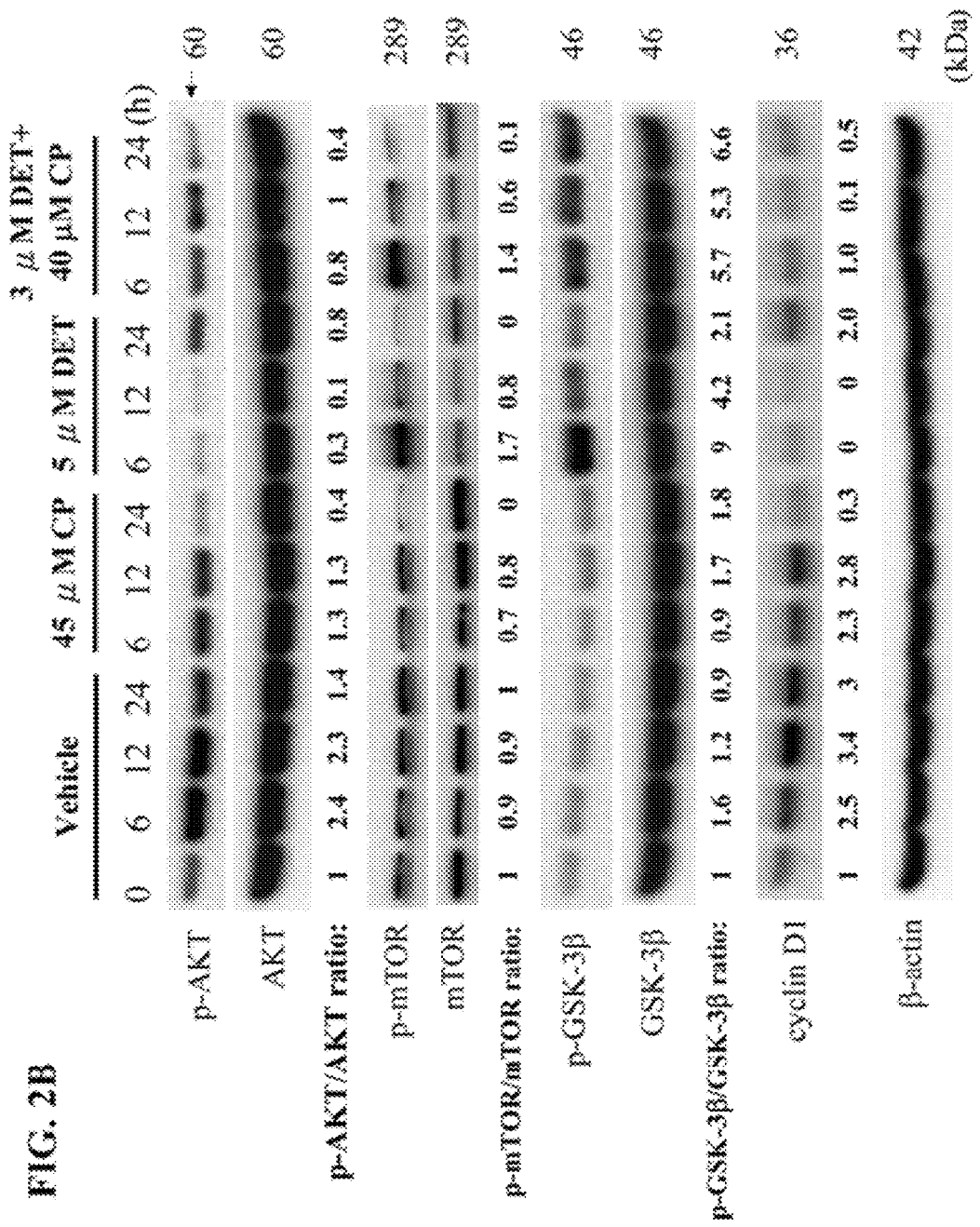
Figure 2C:
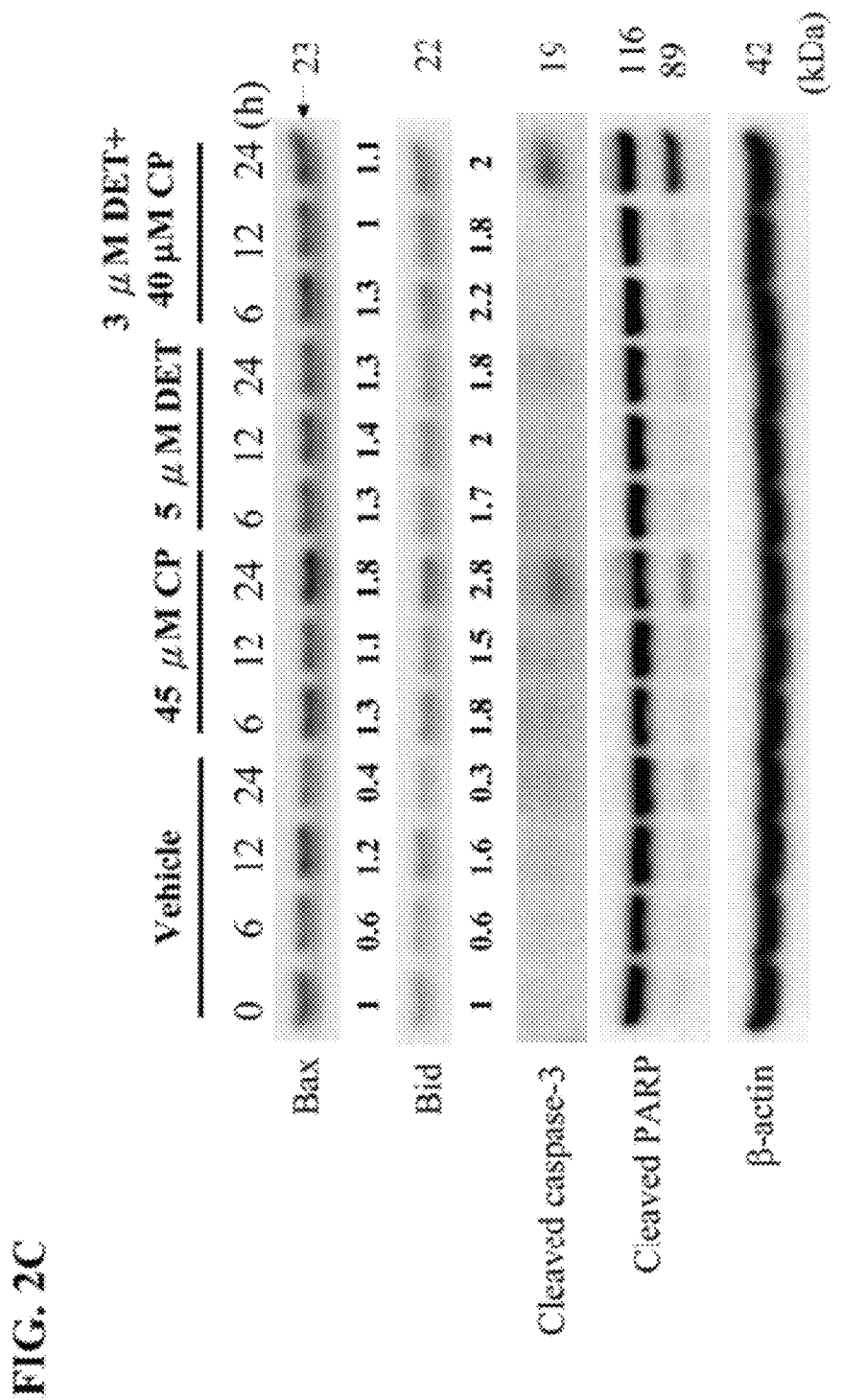

On the other hand, it was also found that cisplatin treatment increase $p27^{kip1}$ expression. DET treatment decreased cdk1 and cyclin A protein expression (FIG. 2A). DET and cisplatin inhibit activities of p-AKT, p-mTOR, p-GSK-3β in B16 melamona cells (FIG. 2B). Cisplatin and combination treatment increased cleaved caspase-3 protein expression and cleaved PARP (FIG. 2C). DET, cisplatin and DET combination with cisplatin treatments increased the sub-$G_1$ (apoptotic) cell fraction to 8.5%, 9% and 24% in B16 melanoma cell, respectively (data not shown).

DET Potentiates the Antitumor Activity of Cisplatin Against Lung Metastasis of B16 Melanoma in Mice The preventive and therapeutic effects of DET or the effect of DET combined with CP or CP and DET sequential treatment on the lung metastasis of B16 melanoma cells in C57BL/6J mice were investigated with CP drug treatment only as a reference control using a non-invasive bioluminescence monitoring system established in this study. The bioluminescence intensity results on Day 21 showed that CP2, DET10+CP1, CP2→DET10, Pre-DET10 and DET10 groups could significant inhibit lung metastasis of B16 cells in C57BL/6J mice, with the mean value of remained bioluminescence intensity of 5%, 11%, 11%, 15% and 49%, respectively, relative to the tumor control group (100%) (P<0.01) (FIG. 4A2). Further, the histopathological examination results showed a typical tissue architecture of lung alveoli in sham control mice, whereas the tumor control group were with significantly grown tumor foci and masses on Day 21, indicating a severe lung metastasis. A much less alveolar defects in lung tissues and relative weight of lung to body weight (%) than tumor group were observed in all treatment groups (FIG. 4B2).

On Day 30, the quantitatively measured bioluminescence photon with respective to tumor growth were found time-dependent in tumor control mice, and the detected mean bioluminescence intensities in the treatment groups were: 2% in CP2, 13% in CP2→DET10, 23% in pre-DET10, 30% in DET10+CP1, and 45% in DET10, compared to tumor group (100%) (FIGS. 4C1 & C2).

DET and Cisplatin Prolong Survival Rate of C57BL/6J Mice

The overall survival time in test mice were measured. It was found that Pre-DET10 and CP2 have similar and most profound effect on extending median survival rate in mice with P<0.05: tumor control: 33 days, Pre-DET10: 43 days, CP2: 43 days, and CP2→DET10: 38 days, DET10: 39 days, DET10+CP1: 36 days (FIG. 4D1). However, CP2 and DET10+CP1 treatment also significantly decreased the body weight of test mice (P<0.05) that was not observed in other treatment groups (FIG. 4D2).

Figure 5A:
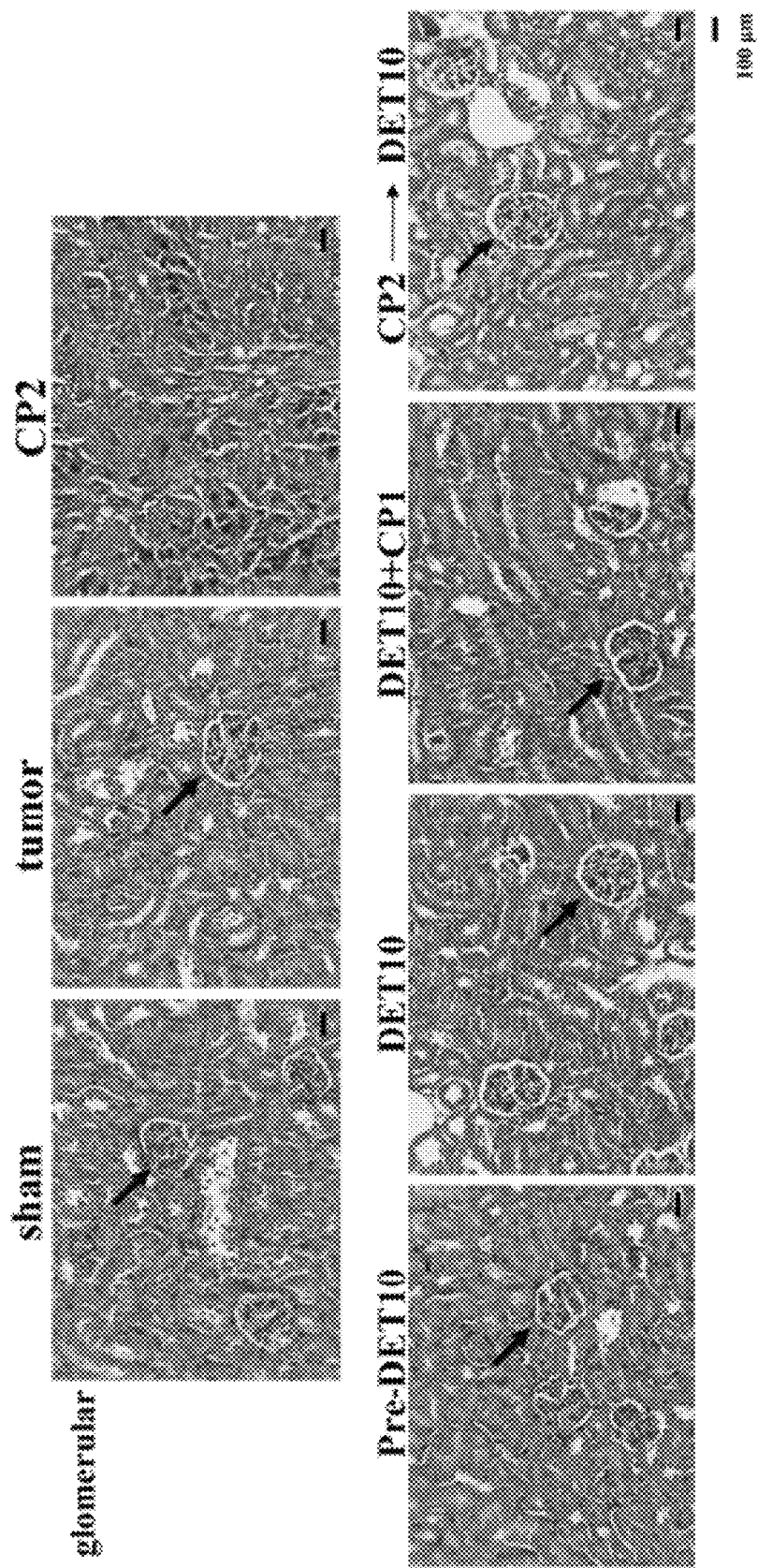
Figure 5B:
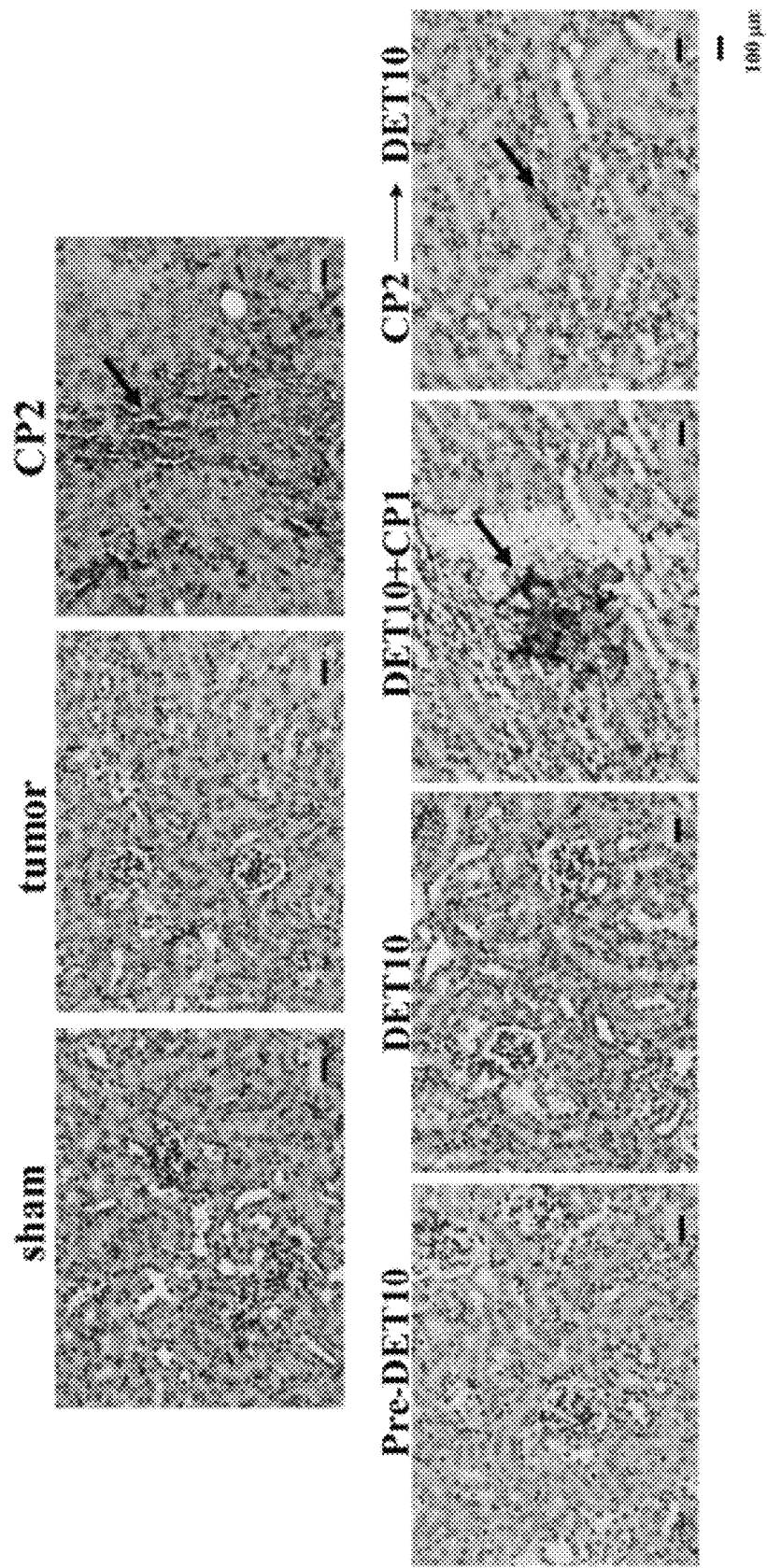

Cisplatin Significantly Induces Kidney Damage and Macrophage Infiltration in Mice FIG. 5A shows that H&E staining of kidney tissues of C57BL/6J mice in sham, tumor control, CP2, Pre-DET10, DET10, DET10+CP1 and CP2→DET10 treatment groups. The results indicate severe glomerular congestion and tubular epithelial atrophy CP2-treated mice. TUNEL assay further demonstrated that TUNEL-positive cells, indicatory apoptotic cells, were observed mostly in the renal tissues of CP2-treated mice, a much less amount in DET10+CP1, very few in sequential treatment (CP2→DET10), and not detectable in Pre-DET10 or DET10 treatment group (FIGS. 5B, 5C1).

The plasma BUN content, an indication of kidney function, was determined in test animals using QuantiChrom™ Urea Kit (BioAssay Systems). The data in FIG. 5C2 shows that at the first week of tumor establishment, the BUN levels were very similar in all of the control and treatment groups, however, CP2 administration significantly induced BUN levels at weeks 2 and 3, indicating a moderate-to-severe degree of renal failure. The sham control, CP2, and DET+CP1 groups had the BUN values of 25.4±4.1 mg/dL, 61.1±4.3 mg/dL, 46.3±4.0 mg/dL on Day 14; and 25.1±4.1 mg/dL, 67.3±0.1 mg/dL, 54.3±7.4 mg/dL on Day 21, respectively. Notably, Pre-DET10 and DET10 groups have little or no detectable changes on the BUN level compared to the sham control group, suggesting no side effect observed in the animals treated with DET.

Macrophage/monocyte infiltration was examined by F4/80 immunostaining in renal tissues of C57BL/6.1 mice. Surprisingly, the macrophage/monocyte infiltration in the renal tissues were found much significant in the CP2-treated mice than that of the control tumor-bearing group, while Pre- DET10, DET10, DET10+CP1 and CP2→DET10 treatment groups have little or no detectable inflammatory cell infiltration (FIGS. 5D1, 5D2).

Cisplatin, but not DET, Causes Haematological Toxicity in C57BL/6J Mice

Complete blood samples of test mice in each group on Day 21 were subjected to the analysis of white blood cell (WBC), neutrophil (N), monocyte (M), basophil (B) red blood cell (RBC), platelet (PLT), hemoglobin (Hb), and hematocrit (Ht) and other cell counts with a hemacytometer (FIG. 10). It was found that the average WBC, M, B, RBC, Hb, Ht, and PLT cell counts in CP2-treated mice were of 24-28%, 33-39%, 41-48%, 65-59%, 67-69%, 65-68%, 52-63%, and 41-52% that of the sham control or tumor-bearing mice without any treatment, whereas, neutrophil populations in the CP2 group were 2.55 and 3.5 times higher than the tumor group and the sham control, respectively. Increase levels of N counts are also observed in DET 10+CP1, CP2→DET10, and DET10 groups, but not in the Pre-DET10 group. In addition, the average WBC ($4.3\pm0.7$ $10^9$/L), RBC ($7.1\pm0.9$ $10^{12}$/L), Hb ($11.3\pm1.6$ g/dl) and Ht ($39.5\pm5.8\%$) and PLT ($343\pm116$ $10^9$/L) counts in the DET10+CP1 treated mice were also lower than those of the sham control. In summary, DET10 treatment alone, especially Pre-DET10, did not cause deleterious effect on the peripheral blood cells profile in C57BL/6J mice. CP2 conferred severe haematological toxicity in mice, and co-treatment or sequential treatment of DET and CP can compromise and reduce part of toxicity caused by CP in the test mice. The data shown in FIG. 10 also shows that only CP2 caused significant spleen damages compared to other groups, as presented by spleen index (weight of spleen (mg)/body weight (g) of test mouse) ($P<0.05$).

Primary Metabolome Analysis of Mouse Renal Tissues Using UPLC/ESI-Q-TOF MS

To address the nephrotoxicity issue of cisplatin treatment and the metabolic alternations that might occur, primary metabolome of renal tissues in the test mice were analyzed by metabolomic approach using UPLC/ESI-Q-TOF MS coupled with principal component analysis (PCA), partial least-squares discriminant analysis (PLS-DA) score plot, loading plot and ingenuity pathway analysis (IPA), and the workflow was schematized in FIG. 9. Three mice kidney tissues in controls (sham or tumor), CP2, Pre-DET10, DET10, DET10+CP1, and CP2→DET10 groups were conducted in UPLC-QTOF MS experimentations. FIG. 6A shows representative UPLC/QTOF total ion chromatograms (TIC) of kidney tissues from controls or treatments, and differences among these TIC profiles were evident. The detected compound peaks in different groups were subjected to further analysis.

The PLA-DA score plot and loading plot of kidney metabolites in various groups of test mice, with 80 and 193 metabolites/compounds detected in positive ion mode and negative ion mode, respectively were analyzed. FIG. 6B shows the results of the score plot and loading plot of the analysis. Distinct clusters of CP group to tumor control and other sham or treatment groups can be seen from the score plot, suggesting the differences of the metabolite profile of the CP group to the others. In FIG. 6C, the loading plot show some distinct metabolites with unknown.

The specific metabolites/compounds in the spectra were verified on the basis of retention time and mass spectra (m/z values) of compounds standards. FIG. 11 summarizes the changes in the contents of 26 identified metabolites in kidney tissues with various treatments. Among them, in comparison with the sham control, the CP-2 treatment caused a decrease (1.7- to 2.4-fold) in alanine, aspartate, phenylalanine, and tryptophan, and an increase in (1.6- to 12.5-fold) pyruvate, citrulline, creatine, uric acid, hippuric acid, and 5-HIAA. The sham control and tumor groups were only different in the content of dodecanoic acid (1.6-fold increase in tumor group), while the pre-DET and DET only caused an increase in pyruvate (1.6-fold), carnitine (2.3-fold) and taurine (2.1-fold), respectively. CP alone or both combinational treatments of DET and CP (DET+CP and CP→DET) groups caused 8.6-fold, 6-fold and 4.8-fold increase, respectively, in 5-HIAA, suggesting DET attenuated the amount of this metabolite induced by CP in the combination treatment. Other significant changes, either increase or decrease, in the metabolites detected in the CP group were not seen in both DET+CP and CP→DET groups of mice. We therefore proposed for primary metabolome networks and related metabolic pathways in mice kidney tissues which were responsive to cisplatin or DET treatment in FIG. 6D.

Discussion

The DET illustrated in the above studies is a major germacranolide SL isolated from *E. scaber*. Compared with parthenolide, DET contains an extra $\alpha,\beta$-unsaturated ketone and $\alpha$-methylene-$\gamma$-lactone without an epoxy group in its structure. DET was first isolated from a different *Elephantopus* species in 1970s. It was demonstrated by the inventor that DET exhibited novel activities against the mammary adenocarcinoma TS/A in cell culture-based experiments and in syngeneic mice.

Interactions between phytoagents, like DET, and chemotherapy drugs, like cisplatin, were assessed by CI analysis. Variable degrees of synergistic cytotoxicity between DET and cisplatin were observed in B16 melanoma cells. Isobologram and CI analyses are the two most popular methods for evaluating drug interactions in combination cancer chemotherapy. Synergistic interactions are of vital importance in phytoagent, which explain the efficacy of apparently low dose of active compounds in herbal medicine. The incorporation of isobologram and CI analyses provides additional qualitative and quantitative information on drug interaction at different combination ratios or concentrations and different effect levels.

Cisplatin causes its cytotoxicity by forming DNA-protein cross links, DNA mono adducts and intrastrand DNA cross links, which all trigger apoptosis. The roles of cyclin-dependent kinase (cdk) and cdk inhibitors, especially p21$^{Waf1/Cip1}$, in cisplatin nephrotoxicity have been demonstrated. The cdk inhibitor, p21, is induced via p53 after DNA damage and plays a key role in stopping the cell cycle at $G_1$/S phase. p21 is a member of the cdk inhibitor protein family that also contains p27$^{kip1}$ (25-27). DET or DET in combination with cisplatin treatment of B16 melanoma cells resulted in inhibition of cyclin A, cyclin B1, and cyclin D1 expression and an increase of the cdk inhibitors p21 and p27. These results can be correlated to the DET and cisplatin induced cycle arrests at $G_2$/M phase (data not shown).

Akt plays a central role in regulating tumor cell survival and cell cycle progression. Akt and mTOR are phosphorylated (activated) in most cancer types. Akt/mTOR is essential for proliferation and survival of malignancies. mTOR, a serine/threonine kinase, integrates various inputs from upstream pathways and plays a central role in regulating cell growth and proliferation. In various cell types, AKT phosphorylates and inhibits glycogen synthase kinase-3$\beta$ (GSK-3$\beta$). GSK-3$\beta$ was phosphorylated at Ser-9. Rossig et at reported that stimulation of AKT increases p21 via inhibitory phosphorylation of GSK-3$\beta$. GSK-3$\beta$ phosphorylates cyclin D1 specifically on Thr286, thereby triggering rapid proliferation regulatory protein (cyclin D1) turnover. GSK-3$\beta$, as a downstream target of AKT, is an important activator of apoptosis, which has been reported to trigger Bax translocation and caspase-3 activation. GSK-3β is constitutively active in unstimulated cells and phosphorylates many proteins such as cyclin D1 to keep it in inactive states or promote it degradation. Induction of p53 leads to increased expression of a large group of p53 regulated proteins, such as cell cycle (p21) and cell death (Bax). It was found that cisplatin treatment induced p53-induced increases in p21 and Bax. In contrast, this was not found in the DET-treated group.

MMPs have been regarded as major molecules that assist tumor cells by cleaving several extracellular matrix (ECM) components during metastasis. On the other hand, cell motility is a complex process requiring coordinated reorganization of actin and microtubule cytoskeletons in physiological and pathological conditions including tumor cell metastasis. It was found that DET and DET combination with cisplatin treatment decrease B16 cell motility and MMP-9 activity.

In order to find the best therapeutic effect on B16 melanoma, the in vivo anti-cancer effect of DET combined with the chemotherapy drug, cisplatin, was examined. A comparative study of the efficacy of DET and cisplatin in C57BL/6J mice showed that Pre-DET10 and CP2 had similar profound effects on inhibiting lung metastasis of B16 melanoma and both increased the median survival rate in tested mice. On the other hand, DET and cisplatin significantly delayed C57BL/6J mice tumor growth, lung metastasis and improved survival rate in vivo. DET alone did not significantly decrease the body weight of mice bearing implanted B16 tumor cells. In contrast, cisplatin treatment group significantly decreased the body weight. It was also demonstrated that DET10+CP1 combination treatment group could recover cisplatin-induced body weight lose.

Histological examination revealed marked tubular damage in the outer medulla in the cisplatin treatment group. It was also found that TUNEL-positive cells located among tubular in the outer stripe of the outer medulla. Cisplantin induced severe macrophages infiltration in kidney tissue in treated mice. DET alone did not significantly decrease WBC, RBC, Hb, Ht, SI of mice bearing implanted B16 tumor cells compared to the cisplatin group, suggesting that DET may not damage the function of the host immune system. The discovery showed that cisplatin alone decreased body weight and the weight Of immune organs (spleen) of mice, DET did not decrease the weight of immune organs. When SI decreased, the weight. of immune organs decreased, and the function of the host immune system was damaged.

In cisplatin injected animals, there was cellular damage in the kidney samples. The rise in the BUN concentration in the serum is used as an important indicator of cisplatin-induced nephrotoxicity. It was discovered that the BUN level increased significantly after cisplatin administration. The histological results also showed that severe degeneration of cortical tubular cells was observed after the cisplatin treatment. This result agreed with the previous studies that have demonstrated the involvement of BUN level in cisplatin-induced nephrotoxicity. Cisplatin treatment is known to potentially cause some renal dysfunctions in cancer patients, such as severe degeneration in glomeruli and both proximal and distal tubuli. It has been reported that coenzyme Q10 treatment ameliorated cisplatin-induced nephrotoxicity in mice.

Multiple lines of evidence suggest that the inflammatory mechanism play an important role in mediating the pathogenesis of cisplatin-induced nephrotoxicity through recruitment of inflammatory cells such as macrophages and leukocytes, which contribute to the cisplatin-induced damage. It has been shown in in vitro studies that cisplatin administration increased macrophage-mediated cytotoxicity against neoplastic cells. Inflammatory cell infiltration into damaged kidney tissue may be an important process in cisplatin-induced renal injury. Infiltrating inflammatory cells may be reservoirs of inflammatory cytokines, chemokines and also release these molecules into damaged kidney tissues. It has been shown in our study that macrophage renal infiltration occurred 72 hours after cisplatin treatment. Renal injury by cisplatin has been associated with oxidative stress, inflammation and apoptosis. Specifically, apoptosis is an important model of cell death in cisplatin nephrotoxicity. It was discovered by the inventor that the number of F4/80-positive cells increased markedly by cisplatin treatment. In contrast, treatment with DET (10 mg/kg for 21 days) caused a significant reduction in the extent of tissue lesions and macrophage infiltration caused by cisplatin nephrotoxicity.

Chemotherapy drugs are typically chemical substances not commonly present in foods and most of them have some kind of side effect or toxicity in the organism. Kidney and liver are the primary targeted sites of drug toxicity. Nephrotoxicity induced by cisplatin was investigated by using kidney metabolic profiling with chemometric analysis. The changes in the metabolic patterns induced by cisplatin were associated with renal disorder and could be identified by a metabonomic method based on UPLC-QTOF mass analysis. Hippuric acid is an acyl glycine formed by the conjugation of benzoic acid with glycine, the amount of hippuric acid is a useful index of liver and kidney function. Hippuric acid is primarily eliminated from the plasma via the kidney by active tubular secretion. Hippuric acid is a harmful uremic toxin that accumulates during renal failure. It has been reported that cyclosporine and sirolimus treatment could induce changes in urine metabolite patterns such as hippurate concentration. It has been reported that the urinary excretion of 5-HIAA, the main metabolite of serotonin, was significantly increased in patients two to six hours after they receive cisplatin chemotherapy. It is also observed in this study that 5-HIAA was obviously increased in cisplatin-treated mice (FIG. 11), however, the reason is not completely clear. Of noted, DET attenuated the amount of 5-HIAA induced by CP in the combination treatment. The metabolic changes suggested the involvement of some specific pathways. The experimental results indicated that metabolomics is a promising new tool for identifying and characterizing biochemical responses to renal toxicity.

Cisplatin is an antineoplastic agent, used in the treatment of a variety of solid tumors that induces severe tubular toxicity. Three distinct segments, S1, S2 and S3 have been described for the proximal tubule of the rat. The S1 and S2 segments make up the pars convolute and are situated in the renal cortex. The S3 segment (pars recta) is located in the outer stripe of the medulla and in the medullary rays. Several other reports have been published on the metabolomic analysis of individual nephrotoxins, such as cisplatin. Cisplatin concentration in proximal tubular cells is about five times the circulating blood level and this disproportionate accumulation of cisplatin in kidney tissue contributes to nephrotoxicity. It has been suggested that the distal tubules were the primary site of apoptosis. Recent studies, however, indicated that proximal tubular cells also undergo apoptosis during cisplatin nephrotoxicity. The side effects of cisplatin, particularly nephrotoxicity, remain a major factor that limits the use and efficacy of cisplatin in cancer therapy.

The findings reported here validated the use of kidney metabolomics screening as a usable strategy to characterize the biochemical perturbation induced by cisplatin toxicity, revealing kidney biomarkers for the toxic effect in kidney and the potential metabolic pathways targeted by the drug. Using this tool, was confirmed the cisplatin toxicity in the kidney. Three biomarkers, hippuric acid, 5-hydroxyindoleacetic acid (5-HIAA) and uric acid were identified and validated to be involved in cisplatin induced nephrotoxicity. In summary, the analysis by UPLC-QTOF mass spectroscopy demonstrates that exposure to cisplatin resulted in a marked change in the kidney metabolic profile that precedes changes in the known biomarkers of nephrotoxicity, such as BUN.

The platinum coordination complex cisplatin, has played a major role in the chemotherapeutic treatment of a variety of neoplasms over the past 25 years. However, the drug possesses significant limitations in being markedly toxic to many normal tissues, especially nephrotoxicities, neurotoxicities and gastrointestinal tract toxicities. The invention relates to the discovery that bioactive compounds from *E. scaber* exhibit potent activity against skin melanoma, with comparable activity to that of cisplatin. Most notable, DET treatment did not cause any detectable side effects as those seen in cisplatin treatment. Instead, when cotreatment of DET with cisplatin, some detected side effects, such as weight loss, shrinkage of the spleen, decreased BUN contents, TUNEL-positive cells and macrophages infiltration in kidney tissue and changed CBC profiles in animals were significantly decreased without affecting the potency on suppression of lung metastasis. These novel pharmacological activities of DET suggest that this phytocompound and its analogues has great potential to be further developed into adjuvant or botanical supplement for the cancer patients with chemotherapy, mainly by decreasing the deteriorated side effect to the patients.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method of treating melanoma, comprising:
   administering to a subject with melanoma a composition comprising:
   (a) a therapeutically effective amount of isolated deoxyelephantopin, isodeoxyelephantopin, scabertopin, isoscabertopin, or any combination thereof; and
   (b) a pharmaceutically acceptable carrier.

2. The method of claim 1, further comprising administering to the subject at least one additional anti-melanoma agent in a therapeutically effective amount.

3. The method of claim 2, wherein the isolated deoxyelephantopin, isodeoxyelephantopin, scabertopin, isoscabertopin, or any combination thereof and the at least one additional anti-melanoma agent are administered sequentially or simultaneously.

4. The method of claim 2, wherein the at least one anti-melanoma agent is selected from the group consisting of cisplatin, betulinic acid, 4-S-cysteaminyl catechol, 4-S-cysteaminyl phenol, everolimus, bortezomib, paclitaxel, carboplatin, dacarbazine, celecoxib, temozolomide, sorafenib, thalidomide, lenalidomide, oxaliplatin, docetaxel, valproic acid, vinblastine, imatinib mesylate, bosentan, doxorubicin, apomine, arsenic trioxide, carmustine, vinblastine and tamoxifen.

5. The method of claim 4, wherein the isolated deoxyelephantopin, isodeoxyelephantopin, scabertopin, isoscabertopin, or any combination thereof is administered to the subject after cisplatin.

6. The method of claim 1, wherein the composition further comprises at least one additional anti-melanoma agent in a therapeutically effective amount.

7. A method of inhibiting proliferation, migration and/or metastasis of melanoma cells, comprising:
   administering to a subject with melanoma a composition comprising:
   (a) a therapeutically effective amount of isolated deoxyelephantopin, isodeoxyelephantopin, scabertopin, isoscabertopin, or any combination thereof; and
   (b) a pharmaceutically acceptable carrier.

8. The method of claim 7, further comprising administering to the subject at least one additional anti-melanoma agent in a therapeutically effective amount.

9. The method of claim 8, wherein the isolated deoxyelephantopin, isodeoxyelephantopin, scabertopin, isoscabertopin, or any combination thereof and the at least one additional anti-melanoma agent are sequentially or simultaneously administered to the subject.

10. The method of claim 8, wherein the at least one additional anti-melanoma agent is cisplatin, and said component (a) reduces the side effect of cisplatin, wherein the side effect is at least one selected from the group consisting of weight loss, spleen shrinkage, decreased BUN contents, TUNEL-positive cells and macrophages infiltration in kidney and changed CBC profiles.

11. A method of treating melanoma, comprising:
    administering to a subject with melanoma a composition comprising:
    (a) an extract of *Elephantopus* species, wherein the extract comprises a therapeutically effective amount of deoxyelephantopin, isodeoxyelephantopin, scabertopin, isoscabertopin, or any combination thereof; and
    (b) a pharmaceutically acceptable carrier.

* * * * *